US012797617B2

(12) United States Patent
Kornet et al.

(10) Patent No.: US 12,797,617 B2
(45) Date of Patent: Nov. 17, 2026

(54) SYSTEMS AND METHODS FOR TREATING MEDICAL CONDITIONS WITH DORSAL ROOT GANGLION STIMULATION

(71) Applicant: Medtronic, Inc., Minneapolis, MN (US)

(72) Inventors: Lilian Kornet, Eijsden (NL); Suryakiran Vadrevu, Santa Clarita, CA (US); Abhijit Bhattacharya, Hyderabad (IN); Maneesh Shrivastav, Blaine, MN (US); ShaileshKumar V. Musley, Brooklyn Park, MN (US); Michael D. Eggen, Chisago City, MN (US)

(73) Assignee: Medtronic, Inc., Minneapolis, MN (US)

( * ) Notice: Subject to any disclaimer, the term of this patent is extended or adjusted under 35 U.S.C. 154(b) by 337 days.

(21) Appl. No.: 18/240,288

(22) Filed: Aug. 30, 2023

(65) Prior Publication Data

US 2023/0405325 A1 Dec. 21, 2023

Related U.S. Application Data

(63) Continuation-in-part of application No. 18/137,378, filed on Apr. 20, 2023, and a continuation-in-part of application No. 18/137,383, filed on Apr. 20, 2023.

(Continued)

(51) Int. Cl.
*A61N 1/36* (2006.01)

(52) U.S. Cl.
CPC ................................ *A61N 1/36135* (2013.01)

(58) Field of Classification Search
CPC ............ A61N 1/36135; A61N 1/36007; A61N 1/36139; A61N 1/3606; A61N 1/36157;

(Continued)

(56) References Cited

U.S. PATENT DOCUMENTS

| | | | |
|---|---|---|---|
| 8,868,185 | B2 | 10/2014 | Zielinski et al. |
| 2005/0065575 | A1 | 3/2005 | Dobak |

(Continued)

FOREIGN PATENT DOCUMENTS

| | | | | |
|---|---|---|---|---|
| CN | 106999709 B | * 7/2021 | | A61N 1/36007 |
| EP | 2651431 B1 | * 3/2018 | | A61N 1/36057 |

OTHER PUBLICATIONS

Candal et al. "Anatomy, Abdomen and Pelvis: Celiac Ganglia," StatPearls Publishing, last updated Aug. 8, 2022, 4 pages [retrieved online Jul. 26, 2023 from: www.ncbi.nlm.nih.gov/books/NBK538129/#article-19097.s1].

(Continued)

*Primary Examiner* — Carl H Layno
*Assistant Examiner* — Mary Grace Schlueter
(74) *Attorney, Agent, or Firm* — Sheridan Ross PC

(57) ABSTRACT

A system comprises a device that includes a signal generator and at least one processor configured to monitor a value of a medical parameter of the patient that is associated with type 2 diabetes, a condition of metabolic syndrome, pancreatis, or any combination thereof. The at least one processor is configured to determine one or more stimulation parameters for stimulating at least one spinal nerve of the patient with an electrical signal, and control the signal generator to generate the electrical signal based on the one or more stimulation parameters. The electrical signal is introduced to the at least one spinal nerve by one or more electrodes, which causes a response by at least one anatomical element of the patient that changes the value of the medical parameter for the patient.

20 Claims, 14 Drawing Sheets

Related U.S. Application Data

(60) Provisional application No. 63/343,217, filed on May 18, 2022, provisional application No. 63/343,196, filed on May 18, 2022.

(58) Field of Classification Search
CPC . A61N 1/0551; A61N 1/36175; A61N 1/0556
USPC ............................................ 607/62, 117, 118
See application file for complete search history.

(56) References Cited

U.S. PATENT DOCUMENTS

| | | | | |
|---|---|---|---|---|
| 2008/0004672 | A1 | 1/2008 | Dalal et al. | |
| 2012/0277839 | A1 | 11/2012 | Kramer et al. | |
| 2016/0045746 | A1 | 2/2016 | Jiang et al. | |
| 2016/0287182 | A1* | 10/2016 | Single | A61B 5/7246 |
| 2017/0296823 | A1* | 10/2017 | Hershey | A61N 1/36139 |
| 2017/0361101 | A1* | 12/2017 | Single | A61N 1/36139 |
| 2019/0321641 | A1* | 10/2019 | Baldoni | A61N 1/36189 |
| 2019/0366094 | A1 | 12/2019 | Esteller et al. | |
| 2020/0368534 | A1* | 11/2020 | Nassif | A61N 1/36125 |
| 2020/0398057 | A1 | 12/2020 | Esteller et al. | |
| 2022/0032058 | A1 | 2/2022 | Kornet et al. | |
| 2023/0372713 | A1 | 11/2023 | Kornet | |
| 2023/0398361 | A1 | 12/2023 | Kornet | |

OTHER PUBLICATIONS

Mizuno et al. "Clinical profile, management, and mortality in very-elderly patients hospitalized with acute decompensated heart failure: An analysis from the ATTEND registry," European Journal of Internal Medicine, Jan. 2016, vol. 27, pp. 80-85.
Official Action for U.S. Appl. No. 18/137,378, dated Jun. 25, 2025 27 pages.
Official Action for U.S. Appl. No. 18/137,383, dated Jun. 13, 2025 24 pages.
Official Action for U.S. Appl. No. 18/137,383, dated Sep. 22, 2025 27 pages.
Official Action for U.S. Appl. No. 18/137,378, dated Oct. 28, 2025 31 pages.
Official Action for U.S. Appl. No. 18/137,378, dated Mar. 12, 2026 27 pages.
Official Action for U.S. Appl. No. 18/137,383, dated Feb. 25, 2026 27 pages.

* cited by examiner

SYSTEMS AND METHODS FOR TREATING MEDICAL CONDITIONS WITH DORSAL ROOT GANGLION STIMULATION

CROSS-REFERENCE TO RELATED APPLICATIONS

The present application is a continuation-in-part of U.S. application Ser. No. 18/137,378, filed on Apr. 20, 2023, and is a continuation-in-part of U.S. application Ser. No. 18/137,383, filed on Apr. 20, 2023, each of which claims the benefit of and priority to U.S. Provisional Application No. 63/343,196, filed on May 18, 2022, entitled "Systems and Methods for Treating Metabolic Syndrome with Dorsal Root Ganglion Stimulation", and U.S. Provisional Application No. 63/343,217, filed on May 18, 2022, entitled "Systems and Methods for Treating Diabetes with Dorsal Root Ganglion Stimulation", all of which are incorporated herein by reference in their entireties.

BACKGROUND

Nerve stimulation is used to treat various conditions, such as pain, by stimulating the nerve with contacts or electrodes. When treating pain, for example, the contacts send an electrical signal generated by an implantable pulse generator to the nerve, which blocks the pain signal from the nerve to the brain.

BRIEF SUMMARY

Example aspects of the present disclosure include:

A system, comprising: a device comprising: a signal generator; and at least one processor configured to: monitor a value of a medical parameter of the patient that is associated with type 2 diabetes, a condition of metabolic syndrome, pancreatis, or any combination thereof, determine one or more stimulation parameters for stimulating at least one spinal nerve of the patient with an electrical signal; and control the signal generator to generate the electrical signal based on the one or more stimulation parameters, the electrical signal being introduced to the at least one spinal nerve by one or more electrodes, which causes a response by at least one anatomical element of the patient that changes the value of the medical parameter for the patient.

Any of the aspects herein, wherein the at least one processor is configured to control the signal generator to generate the electrical signal when the value of the medical parameter is not within an acceptable range of values, and to control the signal generator to cease generating the electrical signal when the value of the medical parameter is within the acceptable range of values.

Any of the aspects herein, wherein the at least one processor controls the signal generator to generate the electrical signal in a manner that keeps the value of the medical parameter within an acceptable range of values.

Any of the aspects herein, wherein the medical parameter being monitored comprises a blood glucose level of the patient, an inflammatory marker associated with pancreatis, or both.

Any of the aspects herein, wherein the at least one processor is configured to select the one or more stimulation parameters further based on activity information about activity of the patient that is known to affect the value of the medical parameter.

Any of the aspects herein, wherein the activity information includes information about past patient activity, current patient activity, predicted patient activity, or any combination thereof.

Any of the aspects herein, wherein the past patient activity includes patient intake of food or patient intake of a drug, wherein the current patient activity includes current patient exercise, and wherein the predicted patient activity includes predicted patient exercise and predicted patient intake of food or predicted patient intake of a drug.

Any of the aspects herein, wherein the at least one processor is configured to select the one or more electrodes, from a group of electrodes, based on compound action potentials (CAPs).

Any of the aspects herein, wherein the at least one processor is configured to select the one or more electrodes based on measurements of CAP conduction velocity and CAP signal amplitude.

Any of the aspects herein, wherein the measurements of CAP conduction velocity and CAP signal amplitude are vectorized measurements.

Any of the aspects herein, wherein the at least one processor is configured to select the one or more electrodes further based on a detected patient position.

Any of the aspects herein, further comprising: the one or more electrodes that stimulate the at least one spinal nerve with the electrical signal; and a monitoring device configured to provide data that enables the at least one processor to monitor the value of the medical parameter.

Any of the aspects herein, wherein the one or stimulation parameters are selected from a list of stimulation parameters.

Any of the aspects herein, wherein the one or more stimulation parameters comprise values for duty cycle of the electrical signal, current level of the electrical signal, frequency of the electrical signal, pulse width of the electrical signal, or any combination thereof.

Any of the aspects herein, wherein the at least one spinal nerve comprises one or more dorsal root ganglions at one or more of thoracic levels T7 thru T12 of the patient, wherein the medical parameter being monitored is one of a glucose level, a triglyceride level, or a cholesterol level, and wherein the response by the anatomical element causes reduction of the glucose level, the triglyceride level, or the cholesterol level.

Any of the aspects herein, wherein the at least one spinal nerve comprises one or more dorsal root ganglions at one or more of thoracic levels T6 thru L2 of the patient, wherein the medical parameter being monitored is a glucose level, an inflammatory marker associated with pancreatis, or both, and wherein the response by the anatomical element causes reduction of the glucose level, the inflammatory marker, or both.

Any of the aspects herein, wherein the response by the anatomical element comprises an increase in insulin production, an increase in urinary excretion, or both.

A system for treating type 2 diabetes, comprising: a device comprising: a signal generator; and at least one processor configured to: monitor a value of a medical parameter of the patient that is associated with type 2 diabetes; determine one or more stimulation parameters for stimulating at least one spinal nerve of the patient with an electrical signal; and control the signal generator to generate the electrical signal based on the one or more stimulation parameters, the electrical signal being introduced to the at least one spinal nerve by one or more electrodes, which causes a response by at least one anatomical element of the patient that changes the value of the medical parameter for the patient.

Any of the aspects herein, wherein the at least one spinal nerve comprises one or more dorsal root ganglions at thoracic levels T9 or T10 of the patient.

A system for treating metabolic syndrome, comprising: a signal generator; and at least one processor configured to: monitor a value of a medical parameter of the patient that is associated with metabolic syndrome; determine one or more stimulation parameters for stimulating at least one spinal nerve of the patient with an electrical signal; and control the signal generator to generate the electrical signal based on the one or more stimulation parameters, the electrical signal being introduced to the at least one spinal nerve by one or more electrodes, which causes a response by at least one anatomical element of the patient that changes the value of the medical parameter for the patient.

Any of the aspects herein, wherein the medical parameter being monitored comprises a level of a lipid level of the patient.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/embodiments in combination with any one or more other aspects/features/embodiments.

Use of any one or more of the aspects or features as disclosed herein.

It is to be appreciated that any feature described herein can be claimed in combination with any other feature(s) as described herein, regardless of whether the features come from the same described embodiment.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as X1-Xn, Y1-Ym, and Z1-Zo, the phrase is intended to refer to a single element selected from X, Y, and Z, a combination of elements selected from the same class (e.g., X1 and X2) as well as a combination of elements selected from two or more classes (e.g., Y1 and Zo).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present disclosure will become apparent to those skilled in the art upon consideration of the embodiment descriptions provided hereinbelow.

BRIEF DESCRIPTION OF THE SEVERAL VIEWS OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

Figure 1:
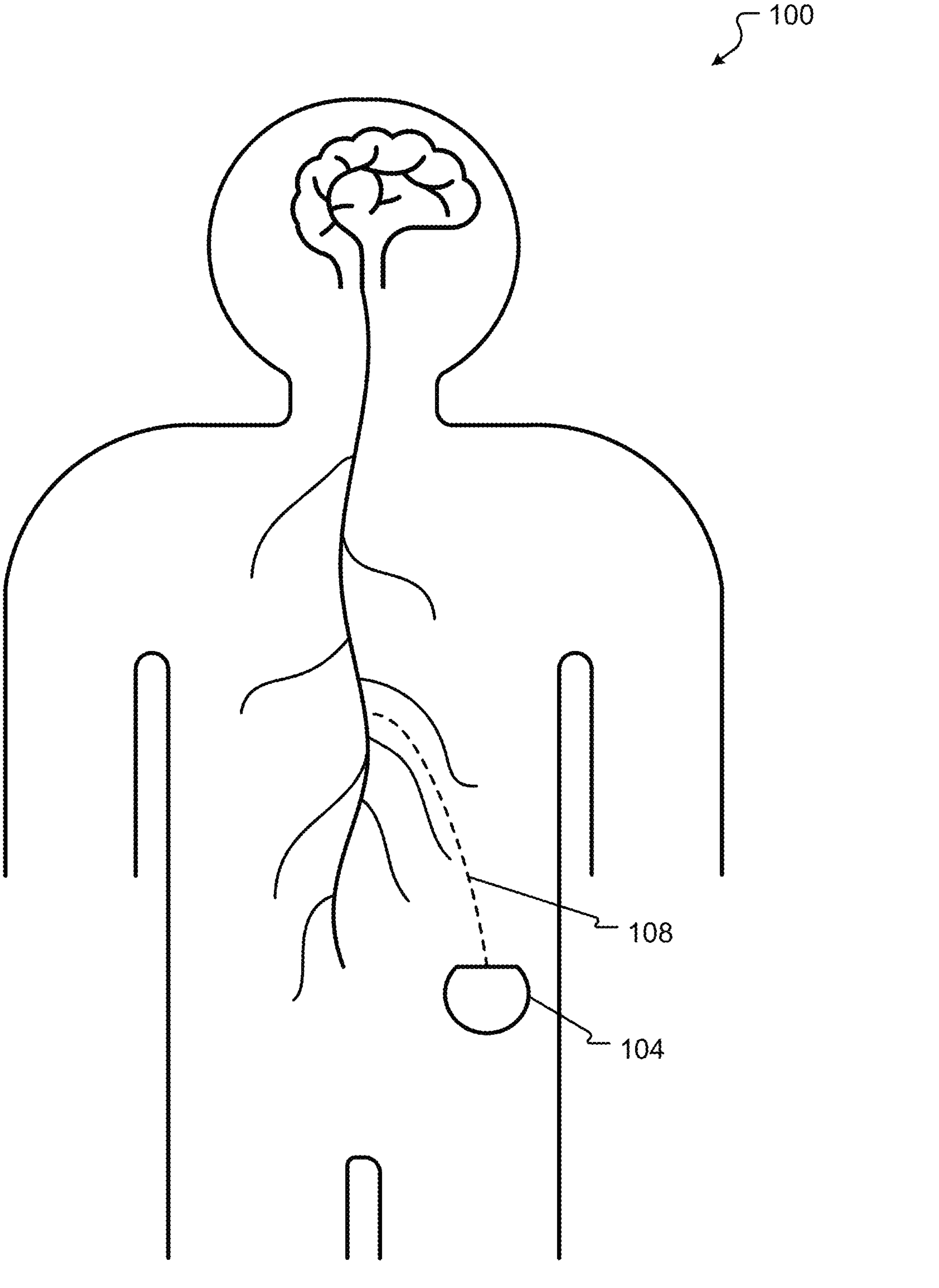
FIG. 1 is a diagram of a system according to at least one embodiment of the present disclosure.

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Alternatively or additionally, functions may be implemented using machine learning models, neural networks, artificial neural networks, or combinations thereof (alone or in combination with instructions). Computer-readable media may include non-transitory computer-readable media, which corresponds to a tangible medium such as data storage media (e.g., random-access memory (RAM), read-only memory (ROM), electrically erasable programmable ROM (EEPROM), flash memory, or any other medium that can be used to store desired program code in the form of instructions or data structures and that can be accessed by a computer).

Instructions may be executed by one or more processing circuits or one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), graphics processing units (e.g., Nvidia GeForce RTX 2000-series processors, Nvidia GeForce RTX 3000-series processors, AMD Radeon RX 5000-series processors, AMD Radeon RX 6000-series processors, or any other graphics processing units), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

Metabolic syndrome may be defined as a cluster of conditions that increase the risk of heart disease, stroke, and type 2 diabetes. These conditions include increased blood pressure, high blood sugar, excess body fat around the waist, and abnormal cholesterol or triglyceride levels. Patients with metabolic syndrome typically receive medication to reduce cholesterol, medication to treat blood glucose, and anti-hypertensive medication. Patients, however, often do not take all their medications. In addition, medications may cause side effects and may have limited efficacy. Inventive concepts propose to address these challenges with techniques that stimulate certain spinal nerves (e.g., dorsal root ganglion nerves; also referred to as dorsal root ganglion(s)) which in turn cases a response by one or more of the patient's organs (e.g., the brain, the liver, and/or pancreas) that helps address at least one condition of metabolic syndrome (e.g., blood pressure, glucose level, cholesterol level, and/or triglyceride level).

In at least one embodiment, for example, a lateral epidural lead is placed near the left and right sides of a patient's spine in areas where multiple dorsal root nerve endings at one or more of thoracic levels T7 thru T12 of the patient can be stimulated with an electrical signal using multiple electrode pairs of the lead. Properties (current, frequency, pulse width, on-off cycling, waveform type, electrode combination (which electrodes are stimulating)) of the electrical signal are selected such that the stimulation of dorsal root ganglions (DRGs) causes one or more organs of the patient to respond in a manner that decreases blood glucose, cholesterol, and/or triglycerides while, in some cases, increasing natriuresis while reducing or preventing side effects like motor stimulation. At least one embodiment relates to a closed loop technique that provides an electrical signal with escalating current values based on blood glucose levels and/or blood pressure.

As may be appreciated, increased glucose levels in the portal vein activates afferent nerve traffic, which results in feedback. The increased DRG activity achieved with stimulation promotes vagal nerve activity to the pancreas and, in this way, promotes insulin production leading to a decrease in blood glucose levels on a systemic level. In addition, the increase in vagal activity and inhibition of sympathetic activity to the liver promotes glycogenesis—the process that converts glucose into glucagon, resulting in lower blood glucose levels. The glucagon is stored in the liver and muscles. In summary, DRG stimulation according to inventive concepts promotes glucogenesis in the liver and insulin release in the pancreas.

In one embodiment, afferent stimulation of DRGs at one or more thoracic levels T7 to T12 mimic signaling afferent information from the pancreas and in this way stimulate sympathetic activation of the pancreas. Additionally, afferent stimulation of DRGs may mimic signaling afferent information from the liver and in this way stimulates sympathetic activation to the pancreas to increase secretion of insulin, which lowers blood glucose. Furthermore, DRG stimulation at one or more thoracic levels T7 thru T12 may also lower blood pressure via 1) the liver's response to the inhibited sympathetic nerves and/or an active vagal nerve and its subsequent action on sodium release, and/or 2) the kidney's response to inhibition of sympathetic activation leading to an increase in urinary excretion and decrease in sodium resorption.

Embodiments of the present disclosure provide technical solutions to one or more of the problems of (1) treating metabolic syndrome with painful injections and/or medication and/or surgery that has limited efficacy and/or aggravating side effects, (2) treating metabolic syndrome by relying on patient cooperation, and (3) undesirable patient outcomes as a result of problems (1) and/or (2).

FIG. 1 illustrates a diagram of aspects of a system 100 according to at least one embodiment of the present disclosure. The system 100 may be used to provide electrical signals for a patient and/or carry out one or more other aspects of one or more of the methods disclosed herein. For example, the system 100 may include at least a device 104 that may be configured to generate a current or electrical signal, such as a signal capable of stimulating one or more nerves (e.g., dorsal root ganglion nerves). In some examples, the device 104 may be referred to as an implantable device. Additionally, the system 100 may include one or more wires or leads 108 that provide a connection between the device 104 and nerves of the patient for enabling nerve stimulation/blocking.

Neuromodulation techniques (e.g., technologies that act directly upon nerves of a patient, such as the alteration, or "modulation," of nerve activity by delivering electrical pulses or pharmaceutical agents to a target area) may be used for assisting in treatments for different diseases, disorders, or ailments of a patient. As described herein, neuromodulation techniques may be used to stimulate one or more nerves which causes a response in one or more anatomical elements of the patient that treats one or more conditions of metabolic syndrome. For example, the device 104 may provide electrical stimulation to one or more nerves in the spinal cord of the patient (e.g., via the one or more leads 108) to cause the brain and subsequently the liver, and/or kidney, and/or pancreas to respond in a manner that treats high blood pressure, diabetes, and/or other conditions of metabolic syndrome. The response by the anatomical element may be directly caused by the stimulation (e.g., stimulation of a nerve causes stimulation of the anatomical element that produces the response) and/or may be indirectly caused the stimulation (e.g., stimulation of a nerve causes the brain to send and/or block signals to an anatomical element that produces the response based on the signals). The response may also include a response that limits intake of food. In one embodiment, stimulating DRGs may activate the vagal nerve and inhibit sympathetic nerves to cause responses in the patient's liver, and/or pancreas, and/or kidney.

In some examples, as shown in FIG. 1, the one or more leads 108 include a single lead 108. In other embodiments, as will be described in FIG. 2, the one or more leads 108 may include multiple leads 208A, 208B. The lead 108 may be implanted on or near a target anatomical element, such as implanted in a location that enables stimulation of one or more DRGs at thoracic levels T7, T8, T9, T10, T11, and/or T12 of the patient. In some examples, the lead 108 is implanted near the spinal cord and more specifically, in the epidural space between the spinal cord and the vertebrae. Once implanted, the lead 108 may provide an electrical signal (whether stimulating or blocking) from the device 104 to the target anatomical element (e.g., one or more nerves in the spinal cord, the brain, etc.). The device 104, in some embodiments, may be implanted in the patient, though in other embodiments—such as during testing of the lead 108—the device 104 may be external to the patient's body.

In some examples, the lead 108 may provide the electrical signals to the respective nerves via electrodes that are connected to the nerves (e.g., sutured in place, wrapped around the nerves, etc.). In some examples, the lead 108 include cuff electrodes (e.g., at an end of the lead 108 not connected or plugged into the device 104). Additionally or alternatively, while shown as physical wires that provide the connection between the device 104 and the one or more nerves, the electrodes may provide the electrical signals to the one or more nerves wirelessly (e.g., with or without the device 104).

Electrodes of a lead 108 may comprise stimulating electrodes (e.g., electrodes configured to stimulate a target anatomical element). In some embodiments, electrodes of a lead 108 may further comprise recording electrodes (e.g., electrodes configured to record a physiological response to the stimulation). The stimulating electrodes may stimulate a target anatomical element such as a nerve and the recording electrodes may record a physiological response to the stimulation. More specifically in closed loop stimulation, the recording electrode may record or measure electrically evoked compound action potential (ECAP), which may be used to regulate or adjust the electrical signal generated by the device 104. For example, as a patient bends over, a distance between the lead 108 and the spinal cord (or other target anatomical element) may change, thus the resulting stimulation may be weaker or stronger based on the change in the distance. The recording electrode may measure and record the ECAPs and a processor may determine a difference in the ECAP. The difference may be used to adjust the electrical signal to cause an amplitude of the ECAP to remain within a range that is comfortable for the patient while still treating a condition of metabolic syndrome.

Additionally, while not shown, the system 100 may include one or more processors (e.g., one or more DSPs, general purpose microprocessors, graphics processing units, ASICs, FPGAs, or other equivalent integrated or discrete logic circuitry) that are programmed to carry out one or more aspects of the present disclosure. In some examples, the one or more processors may be used to drive a feedback loop in a closed-loop stimulation system, as will be discussed in detail with reference to the remaining figures and description. In other examples, the at least one processing circuit may include a memory or may be otherwise configured to perform aspects of the present disclosure. For example, the one or more processors may provide instructions to the device 104, the electrodes, or other components of the system 100 not explicitly shown or described with reference to FIG. 1 for treating metabolic syndrome as described herein. In some examples, the one or more processors may be part of the device 104 or part of a control unit for the system 100 (e.g., where the control unit is in communication with the device 104 and/or other components of the system 100—see, for example, processor 604 in FIG. 6).

The system 100 or similar systems may be used, for example, to carry out one or more aspects of any of the methods described herein. The system 100 or similar systems may also be used for other purposes. It will be appreciated that the human body has many nerves and the stimulation/blocking treatments described herein may be applied to any one or more nerves, which may reside at a suitable location of a patient (e.g., lumbar, thoracic, etc.).

Figure 2:
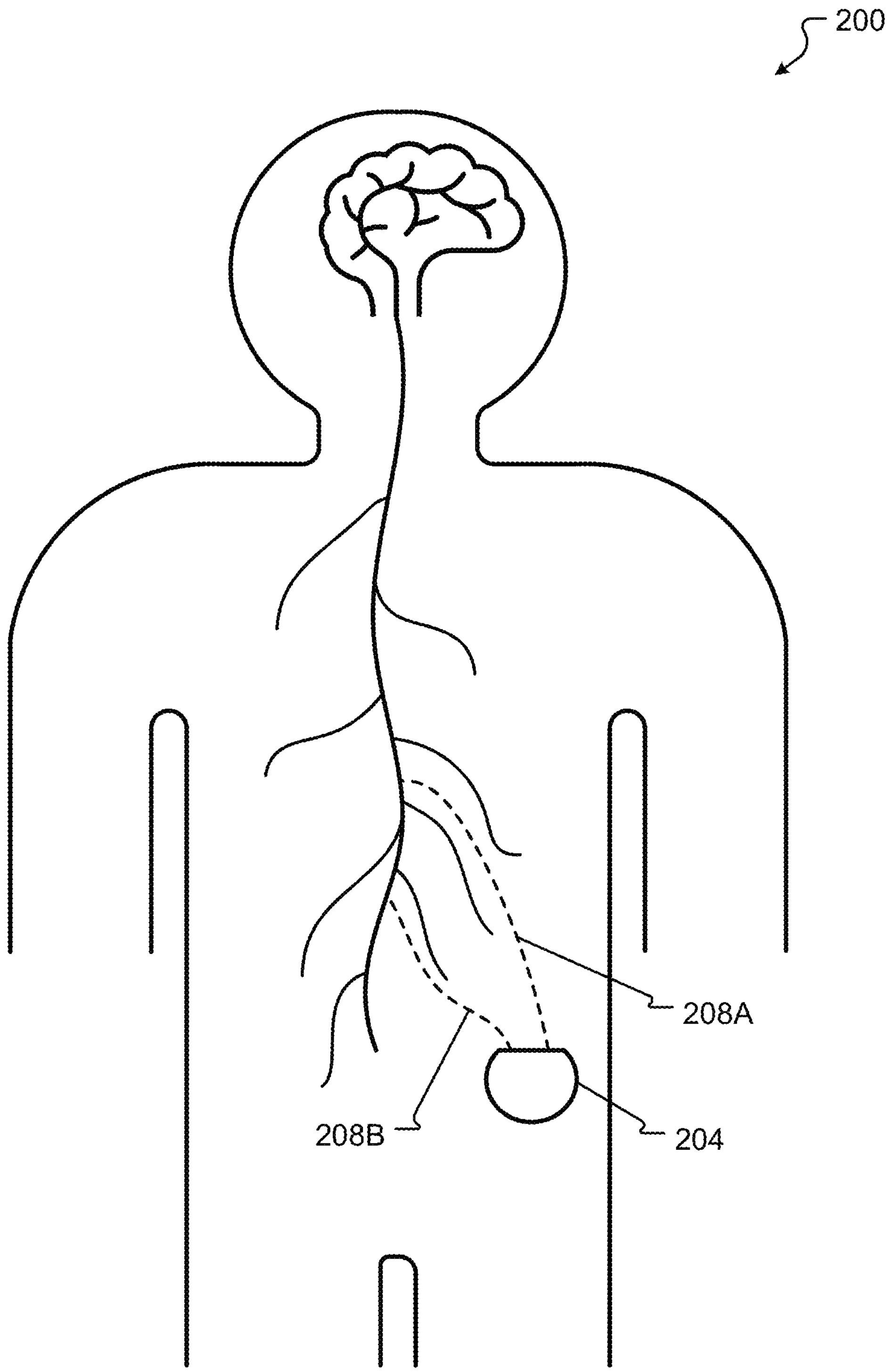
FIG. 2 is a diagram of another system according to at least one embodiment of the present disclosure.

FIG. 2 depicts a system 200 according to at least one embodiment of the present disclosure is shown. The system 200 is the same as or similar to the system 100 and comprises a device 204 which may be the same as or similar to the device 104. The system 200 also includes a lead that comprises a first lead 208A and a second lead 208B. The first lead 208A may comprise stimulating electrodes configured to stimulate a target anatomical element or elements (e.g., DRGs at one side of a spinal cord) and the second lead 208B may comprise additional stimulating electrodes configured to stimulate another target anatomical element or elements (e.g., DRGs at the other side of the spinal cord). The first lead 208A and the second lead 208B may be implanted near each other in in the same space (for example, the epidural space), or may be implanted in separate spaces. It will be appreciated that in some embodiments, the leads 108, 208A, 208B may comprise one lead, two leads, or more than two leads.

Figure 3A:
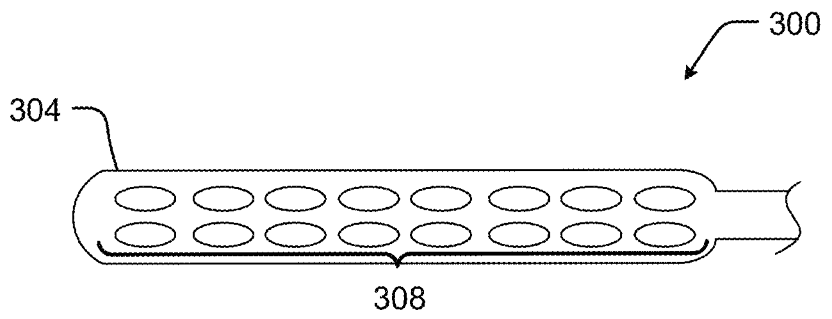
FIG. 3A depicts a schematic illustration of a lead according to at least one embodiment of the present disclosure.
Figure 3B:
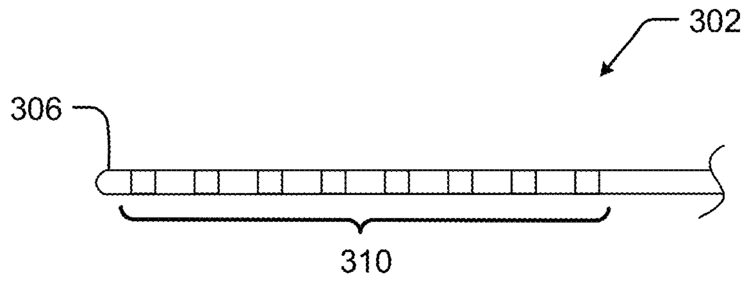
FIG. 3B depicts a schematic illustration of a lead according to at least one embodiment of the present disclosure.

FIG. 3A and FIG. 3B depict a schematic illustration of a first lead 300 and a second lead 302, respectively. The first lead 300, as illustrated, comprises a paddle lead 304 and the second lead 302 comprises a cylindrical lead 306. It will be appreciated that while a paddle lead and a cylindrical lead are shown and described, any type of lead may be used to carry out inventive concepts.

The paddle lead 304 may enable directional stimulation such that stimulation can be directed in a target direction. For example, the paddle lead 304 may be implanted above the spinal cord such that electrodes 308 on the paddle lead 304 face the spinal cord. During stimulation, the electrodes 308 direct the stimulation in the direction of the spinal cord.

The cylindrical lead 306 may also provide directional stimulation when the cylindrical lead 306 is segmented, as described in detail below. Further, the cylindrical lead 306 may be beneficially implanted using a minimally invasive surgical procedure (as opposed to forming an incision to implant the lead). During such procedures, the cylindrical lead 306 can be inserted into the epidural space using an epidural needle.

In the illustrated embodiments, the paddle lead 304 comprises sixteen electrodes 308 and the cylindrical lead 306 comprises eight electrodes 310. It will be appreciated that in other embodiments, the paddle lead 304 may comprise less than or more than sixteen electrodes and the cylindrical lead 306 may comprise less than or more than eight electrodes. Though the electrodes 308 of the paddle lead 304 are shown as ovals, the electrodes 308 (and/or the electrodes 310 of the cylindrical lead 306) may be any shape or size and may be spaced from each other at any distance. Each electrode may also be a different shape or size than another electrode and each electrode may be spaced a different distance from adjacent electrodes. Further, though the electrodes 310 of the cylindrical lead are shown as ring electrodes, the cylindrical lead 306 may be segmented such that the electrodes 310 do not wrap around the entire cylindrical lead 306. More specifically, the cylindrical lead 306 can be segmented into any number of segments. For example, the cylindrical lead 306 can be bi-segmented or tri-segmented. In a segmented cylindrical lead 306, the electrode can be positioned in a segment such that the electrode will direct the stimulation in the direction that the electrode is facing. In other words, a segmented cylindrical lead 306 may enable directional stimulation in a target direction toward a target nerve.

Figure 4A:
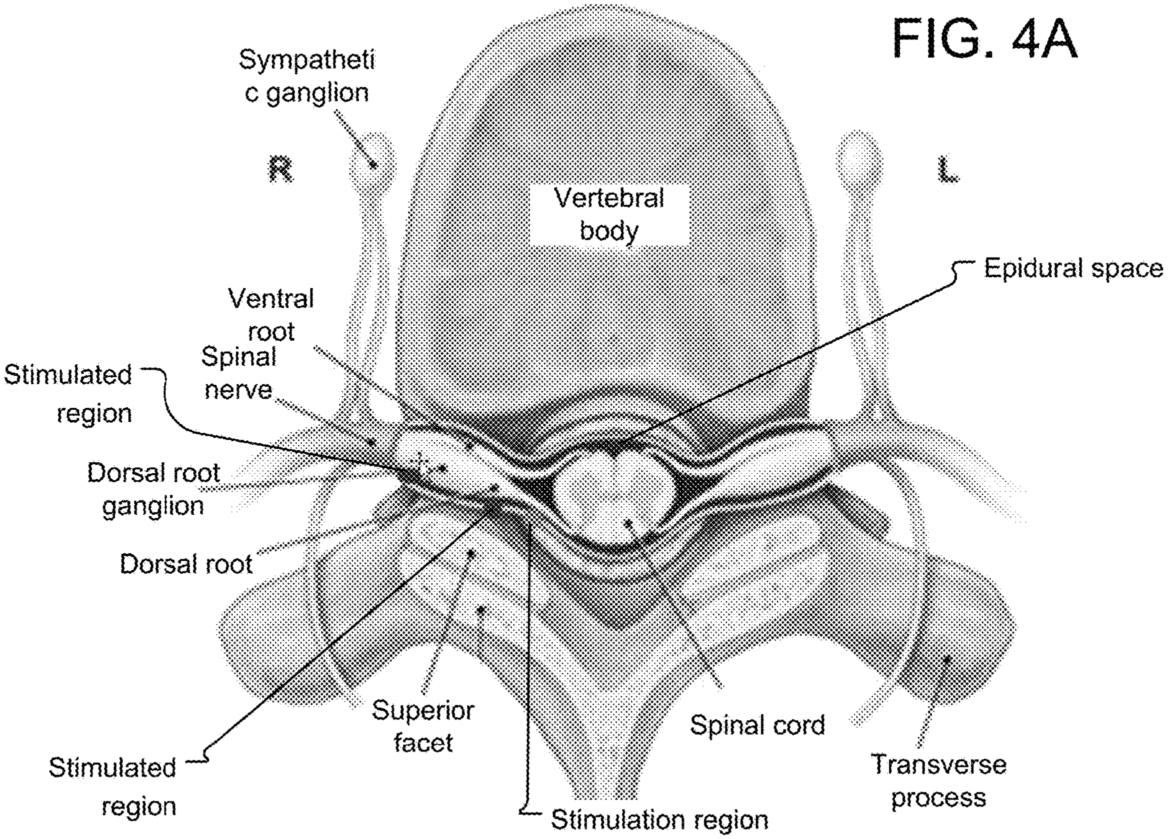
FIGS. 4A to 4C illustrate various views of spinal anatomy for explaining nerve stimulation according to at least one embodiment of the present disclosure.
Figure 4B:
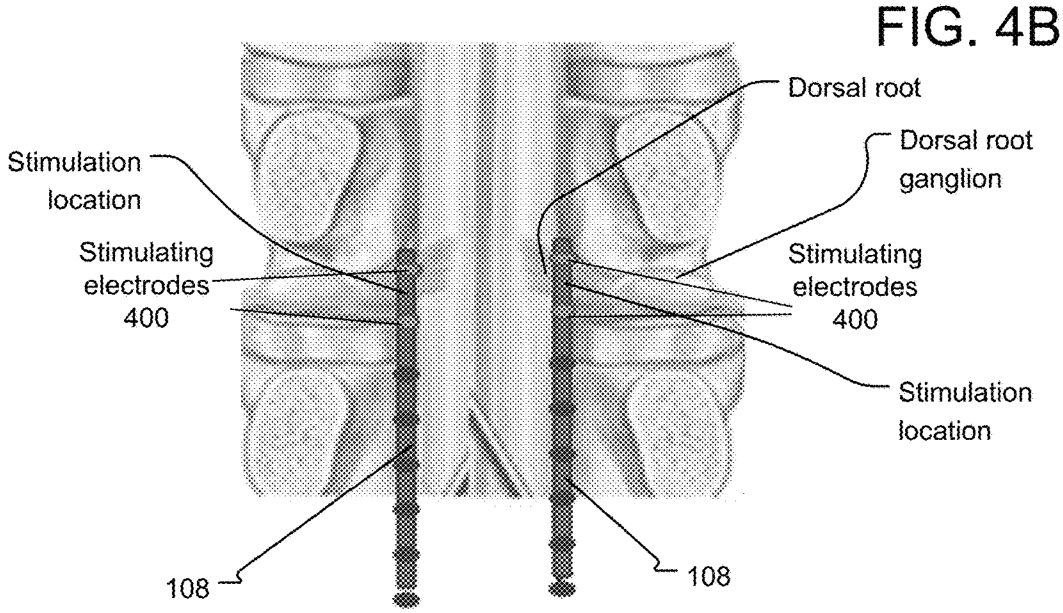

FIG. 4A illustrates a cross-sectional view of a spine that shows possible stimulated regions of a nerve according to at least one example embodiment. The view in FIG. 4A may correspond to a cross-section taken at thoracic level T10 from below. Meanwhile, FIG. 4B illustrates a view showing a pair of epidural leads 108 implanted at the left and right sides of a patient's spine, where each lead 108 includes a pair of stimulating electrodes 400. FIGS. 4A and 4B illustrate various anatomical elements of the spine including a vertebral body, epidural space, transverse processes, spinal cord, superior facets, sympathetic ganglions, a spinal nerve, ventral roots, dorsal roots, and dorsal root ganglions. FIG. 4A further illustrates stimulated regions on a right side R of the vertebral body. Although not explicitly shown, it should be appreciated that the stimulated regions exist in the same corresponding locations at a left side L of the vertebral body. A stimulation location in FIG. 4B may correspond to a location at which or near which one or more electrodes are implanted. As shown, the stimulation location corresponds to or is proximate to the dorsal root while the stimulated regions correspond to the dorsal root and/or the dorsal root ganglion.

FIG. 4B shows a set of electrodes that includes two pairs of stimulating electrodes 400 on two leads 108 that are positioned in a location that enables injection of an electrical signal at or near the stimulation location of the left and right sides of the vertebral body. Each pair of stimulating electrodes 400 may receive the electrical signal from a signal generator (e.g., signal generator 616 in FIG. 6) of the device 104 which in turn stimulates the dorsal root ganglion at the left and right sides of the vertebral body. In the example shown in FIG. 4B, each pair of stimulating electrodes 400 comprises one electrode at a top side of the dorsal root and one electrode at a bottom side of the dorsal root with each electrode receiving an electrical signal from a signal generator of the device 104. As shown, the stimulation location in FIG. 4B may be under or directly adjacent to a lead 108 between a pair of stimulating electrodes 400 in a lengthwise direction of the lead 108. In at least one embodiment, each stimulating electrode 400 may be about 1.5 mm in size and be within about 5 mm (+/−20%) of the dorsal root. Using an electrode configuration with pairs of stimulating electrodes 400 as shown in FIG. 4B may assist with focusing electrical energy to the stimulation location between a pair of stimulating electrodes 400. However, example embodiments are not limited to using pairs of electrodes to stimulate a dorsal root ganglion, and a single stimulating electrode on each lead 108 may be placed at or near the stimulation location on each side of the vertebral body to stimulate a respective dorsal root ganglion. Notably, the stimulating electrodes 400 may be passively held in place by surrounding tissue of the patient and should be located at a position that does not accidentally stimulate the ventral root (which may cause negative side effects for the patient). As may be appreciated, remaining electrodes (i.e., non-stimulating electrodes) of each lead 108 do not receive the electrical signal for the purpose of treating one or more conditions of metabolic syndrome. However, depending on locations of the remaining electrodes, the remaining electrodes may receive electrical signals for other purposes (e.g., for treating another condition, like pain).

Figure 4C:
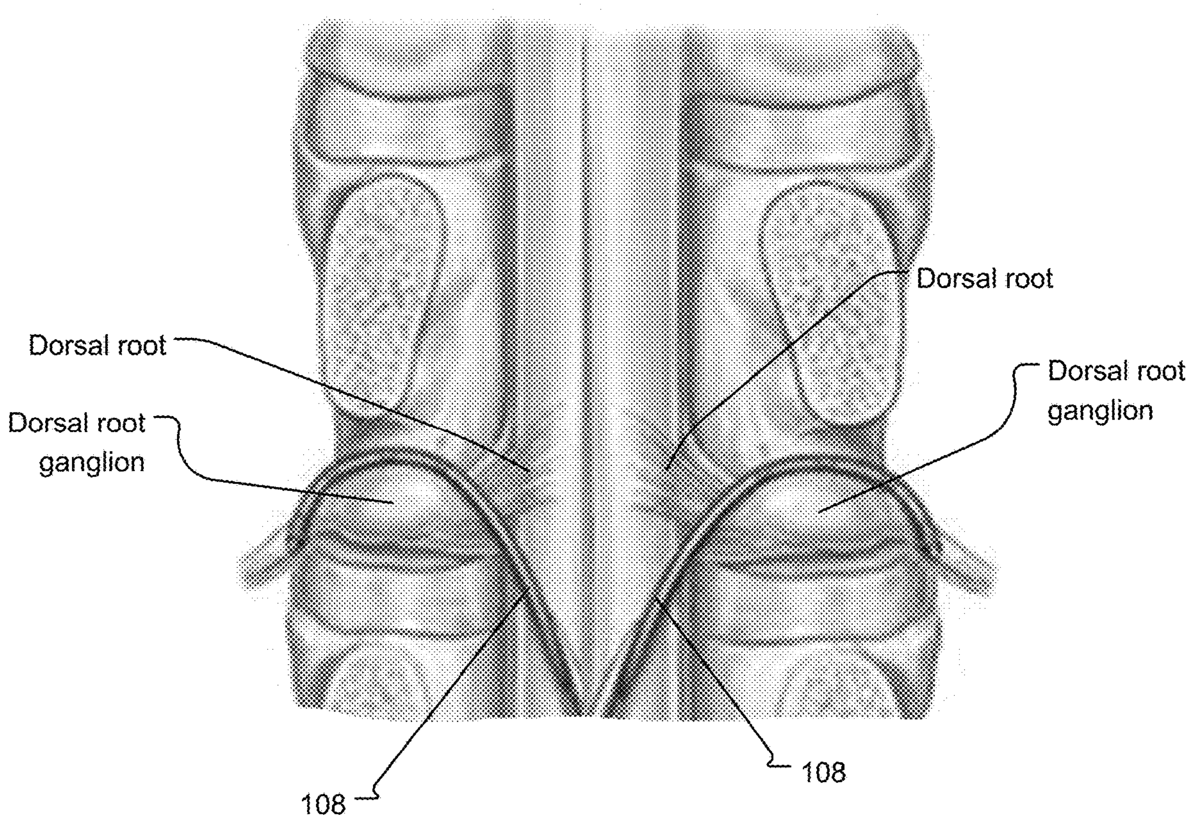

FIG. 4C illustrates another example configuration for leads 108 according to at least one example embodiment. As shown in FIG. 4C, each lead 108 may have curved structure designed to conform to or partially conform to a shape of a respective DRG so that one end of each lead 108 terminates at an outer part of the respective DRG while a section of the lead 108 curves around one edge of the respective DRG. Although not explicitly shown, each lead 108 in FIG. 4C may include a set of electrodes spaced apart from one another along the length of the lead 108 as in FIGS. 3A, 3B, and 4B. As in FIG. 4B, each lead 108 in FIG. 4C may include one or more stimulating electrodes to stimulate a respective DRG with an electrical signal from device 104 while other electrodes on each lead 108 may remain inactive.

In accordance with example embodiments, stimulating the dorsal root ganglions may cause one or more responses by one or more anatomical elements of the patient that helps treat at least one condition of metabolic syndrome, such as blood pressure, glucose level, cholesterol level, and/or triglyceride level. For example, dorsal root ganglion stimulation may cause a response by the liver that promotes glucogenesis to reduce blood glucose level, and/or a response by the pancreas that promotes insulin production, and/or a response of the kidney or liver that results in lowering blood pressure. These responses may result from inhibiting sympathetic nerves and activating the vagal nerve when DRGs are stimulated. As noted above, the response by the liver, kidney, and/or pancreas may be the result of indirect stimulation (e.g., stimulation of DRGs causes the brain to send and/or block signals to the liver, and/or pancreas, and/or kidney that produce the responses based on the signals).

Although FIGS. 4A and 4B have been described with reference to a single thoracic level (e.g., level T10), additional leads 108 with pairs of stimulating electrodes 400 may be implanted at the same or similar locations to achieve the same or similar stimulation effects at one or more other thoracic levels, for example, at one more of T7, T8, T9, T11, and/or T12 levels.

Figure 5:
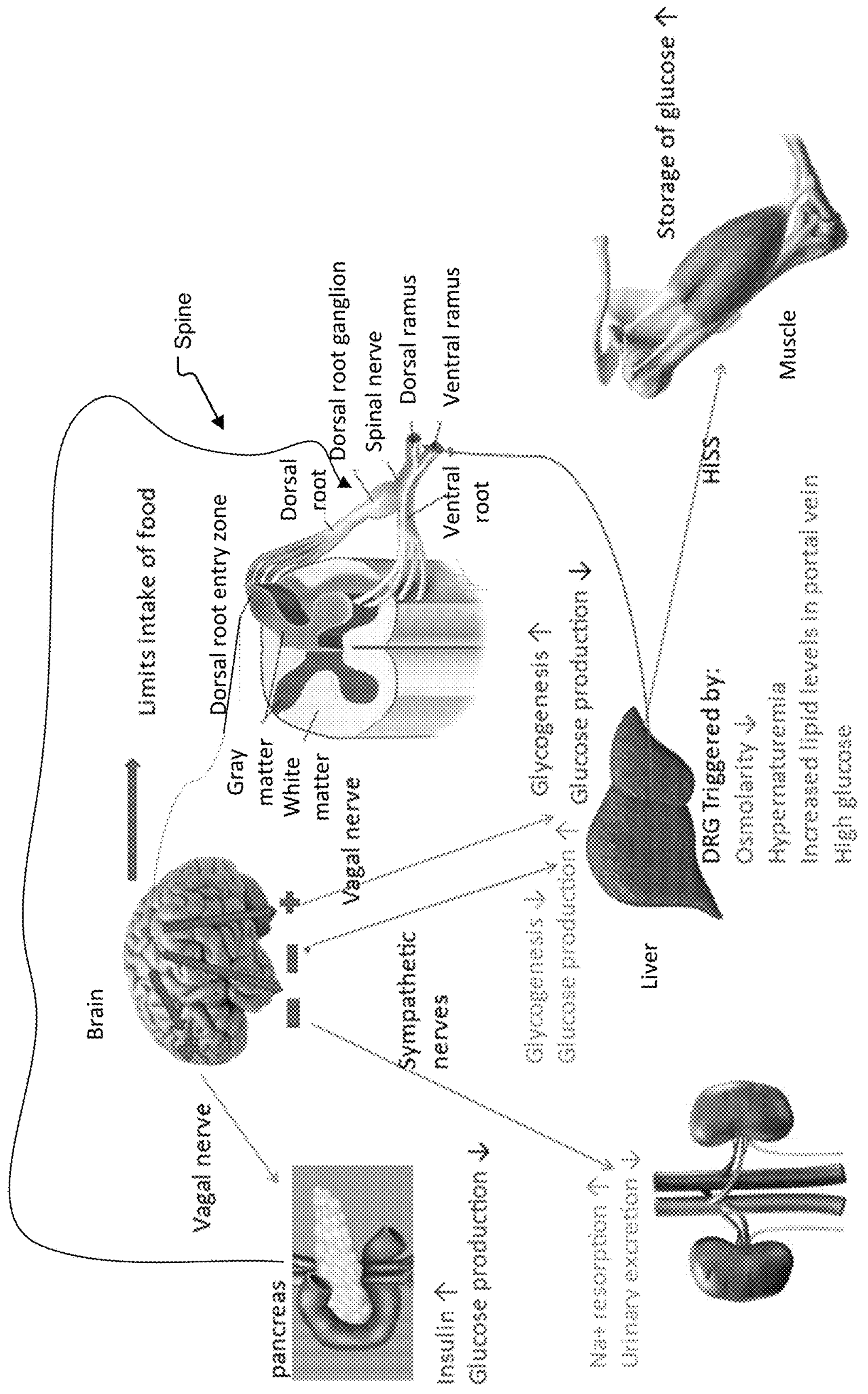
FIG. 5 is a diagram that illustrates various physiological effects/relationships for certain anatomical elements according to at least one embodiment of the present disclosure.

FIG. 5 is a diagram that illustrates various physiological effects/relationships for certain anatomical elements. As shown, activation of sympathetic nerves increases sodium resorption and reduces urinary excretion by the kidneys while also decreasing glycogenesis and increasing glucose production by the liver. Meanwhile, activation of the vagal (or vagus) nerve increases insulin production, decreases glucose production in the pancreas and increases glycogenesis and reduces glucose production in the liver. As may be appreciated, DRG stimulation according to example embodiments inhibits sympathetic nerves and activates the vagal nerve, which results in lower glucose production and increased glycogenesis while limiting food intake. In addition, DRG stimulation may cause release of a hepatic insulin sensitizing substance (HISS) from the liver to increase glucose storage in muscle. In one embodiment, DRG stimulation at spinal level T12 may affect feedback.

Figure 6:
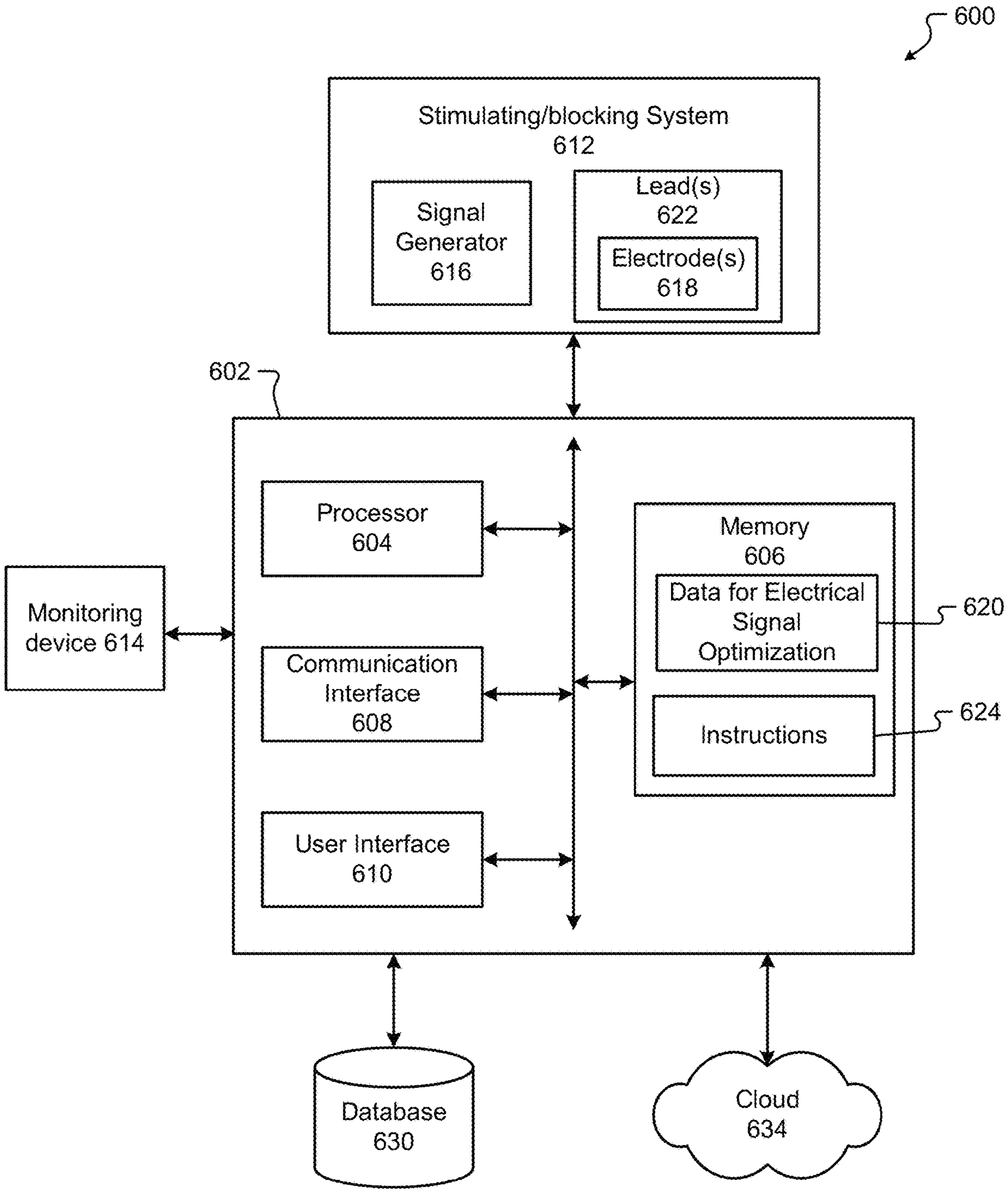
FIG. 6 is a block diagram of a system according to at least one embodiment of the present disclosure.

FIG. 6 depicts a block diagram of a system 600 according to at least one embodiment of the present disclosure. In some examples, the system 600 may implement aspects of or may be implemented by aspects of FIGS. 1-5 as described herein. For example, the system 600 may include a computing device 602, a monitoring device 614, and a stimulating/blocking system 612 with a signal generator 616 and/or one or more lead(s) 622 to carry out one or more aspects of one or more of the methods disclosed herein. A device 104, 204 as described with reference to FIGS. 1 and 2 may include aspects of the system 600, such as the signal generator 616, the computing device 602, and/or the monitoring device 614. In this case, the signal generator 616 and the computing device 602 may be integrated with one another in the same implantable device 104, 204. The lead(s) 622 may represent an example of the lead(s) 108, 208, 300, and/or 302 from FIGS. 1-3B. The system 600 may further comprise a database 630, and/or a cloud or other network 634. Systems according to other embodiments of the present disclosure may comprise more or fewer components than the system 600. For example, the system 600 may not include one or more components of the computing device 602, the database 630, and/or the cloud 634.

The stimulating/blocking system 612 may comprise the signal generator 616 and the lead(s) 622. As previously described, the signal generator 616 may be configured to generate an electrical signal, and the lead 622 may comprise a plurality of electrodes 618 configured to apply the electrical signal to a target anatomical element (e.g., DRG(s)). The electrodes 618 may correspond to electrodes of leads 108 described herein and may include stimulating electrodes and, in some cases, non-stimulating electrodes. The stimulating/blocking system 612 may communicate with the computing device 602 to receive instructions such as instructions 624 for applying the electrical signal to the target anatomical element, where the electrical signal is intended to stimulate one or more DRGs at one or more thoracic levels from T7 to T12 to thereby generate a response by at least one anatomical element such as the brain, liver, and/or pancreas.

The computing device 602 is illustrated to include a processor 604, a memory 606, a communication interface 608, and a user interface 610. Computing devices according to other embodiments of the present disclosure may comprise more or fewer components than the computing device 602.

The processor 604 of the computing device 602 may comprise one or more suitable processing circuits such as one or more suitable processors described herein or any similar suitable processor. The processor 604 may be configured to execute instructions 624 stored in the memory 606, which instructions may cause the processor 604 to carry out one or more methods described herein. For example, as described in more detail below, the processor 604 may execute instructions 624 to monitor a parameter of a patient, such as a blood glucose level, and to control generation of the electrical signal by the signal generator 616 based on the monitored parameter and a threshold associated with the monitored parameter (e.g., a threshold blood glucose level).

The memory 606 may be or comprise RAM, DRAM, SDRAM, other solid-state memory, any memory described herein, or any other tangible, non-transitory memory for storing computer-readable data and/or instructions. The memory 606 may store information or data useful for completing, for example, any steps of the methods described herein, or of any other methods. The memory 606 may store, for example, instructions and/or machine learning models that support one or more functions of the stimulating/blocking system 612. For instance, the memory 606 may store content (e.g., instructions 624 and/or machine learning models) that, when executed by the processor 604, cause the signal generator 616 to generate an electrical signal for lead(s) 622 which apply the electrical signal to a respective target anatomical element such as a DRG to cause a response in one or more anatomical elements that changes a value of the parameter being monitored to treat a condition of metabolic syndrome.

The memory 606 may also store data for electrical signal optimization 620. Data for electrical signal optimization 220 may correspond to a routine executed by the processor 604 to optimize the electrical signal used in an electrical stimulation. Optimization may be achieved by adjusting signal current, adjusting signal amplitude, adjusting signal frequency, adjusting signal type (e.g., square wave, sinusoidal wave, triangle wave, etc.), adjusting duty cycle, adjusting treatment duration, electrode combination (e.g., which electrodes are stimulating), signal polarity (positive or negative), and/or the like. More specifically, the electrical signal optimization 620 may enable the processor 604 to determine one or more parameters of the electrical signal. Data for electrical signal optimization 620 may also enable the processor 604 to determine or adjust one or more parameters of the electrical signal based on a physiological response recorded during stimulation of the target anatomical element. The one or more parameters of the electrical signal may be adjusted to, for example, maintain one or more monitored parameters of the patient within an acceptable range. For example, as discussed in more detail below, current of the electrical signal may be gradually increased over time to bring a patient parameter (e.g., blood glucose) below a threshold value to treat one or more conditions of metabolic syndrome. The data for electrical signal optimization 620 may be preprogrammed before or shortly after implantation of a device 104, 204, but may change as the computing device 602 learns more about which parameters of the electrical signal and/or other parameters of the treatment process result in better treatment of metabolic syndrome for a particular patient. For example, parameters related to treatment duration, current of the electrical signal, pulse width of the electrical signal, and/or frequency of the electrical signal may have initial values that are adjusted over time to better treat metabolic syndrome and saved as data for electrical signal optimization 620 (see, e.g., step 724 below). In addition, parameters may be optimized in a way that prevents glucose levels from becoming too low, causing hypoglycemia, which can be life threatening.

Content stored in the memory 606, if provided as instructions, may be organized into one or more applications, modules, packages, layers, or engines. Alternatively or additionally, the memory 606 may store other types of content or data (e.g., machine learning models, artificial neural networks, deep neural networks, etc.) that can be processed by the processor 604 to carry out the various method and features described herein. Thus, although various contents of memory 606 may be described as instructions, it should be appreciated that functionality described herein can be achieved through use of instructions, algorithms, and/or machine learning models (e.g., for electrical signal optimization). The data, algorithms, and/or instructions may cause the processor 604 to manipulate data stored in the memory 606 and/or received from or via the stimulating/blocking system 612, the database 630, and/or the cloud 634.

The computing device 602 may also comprise a communication interface 608. The communication interface 608 may be used for receiving data (for example, data from a recording electrodes capable of recording data) or other information from an external source (such as the stimulating/blocking system 612, the database 630, the cloud 634, and/or any other system or component not part of the system 600), and/or for transmitting instructions, images, or other information to an external system or device (e.g., another computing device 602, the stimulating/blocking system 612, the database 630, the cloud 634, and/or any other system or component not part of the system 600). The communication interface 608 may comprise one or more wired interfaces (e.g., a USB port, an Ethernet port, a Firewire port) and/or one or more wireless transceivers or interfaces (configured, for example, to transmit and/or receive information via one or more wireless communication protocols such as 802.11a/b/g/n, Bluetooth, NFC, ZigBee, and so forth). In some embodiments, the communication interface 608 may be useful for enabling the device 602 to communicate with one or more other processors 604 or computing devices 602, whether to reduce the time needed to accomplish a computing-intensive task or for any other suitable reason.

The computing device 602 may also comprise one or more (optional) user interfaces 610. The user interface 610 may be or comprise a keyboard, mouse, trackball, monitor, television, screen, touchscreen, and/or any other device for receiving information from a user and/or for providing information to a user. The user interface 610 may be used, for example, to receive a user selection or other user input regarding any step of any method described herein. In some embodiments, the user interface 610 may be used to select one or more parameters for the electrodes including, but not limited to, selecting whether an electrode is active or inactive. For example, the user interface 610 may receive input to select a first electrode as active and to select a second and a third electrode as inactive. Notwithstanding the foregoing, any required input for steps of methods described herein may be generated automatically by the system 600 (e.g., by the processor 604 or another component of the system 600) or received by the system 600 from a source external to the system 600. In some embodiments, the user interface 610 may be useful to allow a surgeon or other user to modify instructions to be executed by the processor 604 according to one or more embodiments of the present disclosure, and/or to modify or adjust a setting of other information displayed on the user interface 610 or corresponding thereto.

Although the user interface 610 is shown as part of the computing device 602, in some embodiments, the computing device 602 may utilize a user interface 610 that is housed separately from one or more remaining components of the computing device 602. In some embodiments, the user interface 610 may be located proximate one or more other components of the computing device 602, while in other embodiments, the user interface 610 may be located remotely from one or more other components of the computer device 602. In this case, the communication interface 608 may enable communication between the computing device 102 and the user interface 610.

The monitoring device 614 may include suitable hardware and/or software for monitoring at least one parameter of a patient that is useful for determining whether DRG stimulation is effectively treating one or more conditions of metabolic syndrome. The monitoring device 614 may continuously provide data that enables the processor 604 to monitor the value of the at least one parameter of the patient. The monitoring device 614 may be attachable to and/or or at least partially implanted in a patient. In one non-limiting example, the monitoring device 614 comprises a blood glucose monitor that monitors a blood glucose level of the patient. Another non-limiting example of a monitoring device 614 may include a blood pressure monitor, which may be incorporated into a wearable such as a fitness tracker or fitness watch. In other embodiments, the monitoring device 614 may include a device that monitors the patient's cholesterol levels, and/or triglyceride levels. Still further, the monitoring device 614 may comprise a device that monitors the status of (e.g., the amount of) body fluids, for example, with a suitable impedance sensor because stimulating DRGs may affect the splanchnic bed which, in turn, affects body fluid status and/or blood pressure. The monitoring device 614 may include additional or alternative devices that monitor any suitable parameter useful for determining whether DRG stimulation is successfully treating a condition of metabolic syndrome in the patient. The monitoring device 614 may be separate from the device 104, 204 in FIGS. 1 and 2 while being in wired or wireless communication with the computing device 602. In one embodiment, the monitoring device 614 is integrated with the device 104, 204 along with the stimulating/blocking system 612 and/or the computing device 602.

The database 630 may store information such as patient data, results of a stimulation and/or blocking procedure, stimulation and/or blocking parameters, electrical signal parameters, electrode parameters, electrode configurations and/or the like. The database 630 may be configured to provide any such information to the computing device 602 or to any other device of the system 600 or external to the system 600, whether directly or via the cloud 634. In some embodiments, the database 630 may be or comprise part of a hospital image storage system, such as a picture archiving and communication system (PACS), a health information system (HIS), and/or another system for collecting, storing, managing, and/or transmitting electronic medical records.

The cloud 634 may be or represent the Internet or any other wide area network. The computing device 602 may be connected to the cloud 634 via the communication interface 608, using a wired connection, a wireless connection, or both. In some embodiments, the computing device 602 may communicate with the database 630 and/or an external device (e.g., a computing device) via the cloud 634.

The system 600 or similar systems may be used, for example, to carry out one or more aspects of any of the method 700 as described herein. The system 600 or similar systems may also be used for other purposes.

Figure 7:
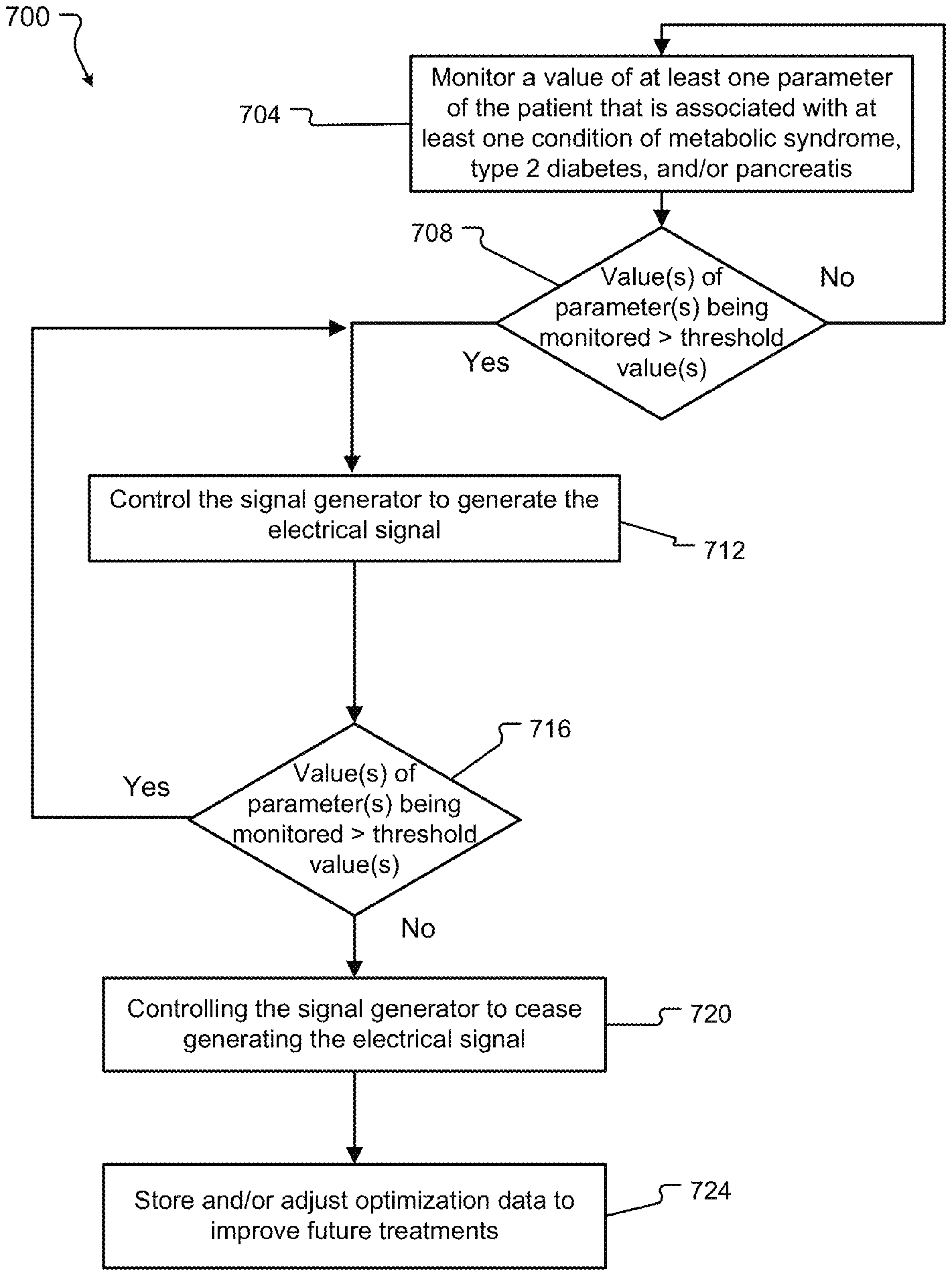
FIG. 7 is a flowchart according to at least one embodiment of the present disclosure.

FIG. 7 depicts a method 700 that may be used, for example, to perform neuromodulation techniques (e.g., a stimulation/block therapy) to treat at least one condition of metabolic syndrome for a patient.

The method 700 (and/or one or more steps thereof) may be carried out or otherwise performed, for example, by at least one processor. The at least one processor may be the same as or similar to the processor 604 or the processor(s) of the device 104 or 204 described above. The at least one processor may be part of the device 104 or 204 (such as an implantable pulse generator) or part of a control unit in communication with the device 104 or 204. A processor other than any processor described herein may also be used to execute the method 700. The at least one processor may perform the method 700 by executing elements stored in a memory (such as a memory 606 in the device 104 as described above). The elements stored in the memory and executed by the processor may cause the processor to execute one or more steps of a function as shown in method 700. One or more portions of a method 700 may be performed by the processor executing any of the contents of memory, such as providing stimulation to a nerve with an electrical signal, executing an electrical signal optimization such as the electrical signal optimization 620, and/or any associated operations as described herein.

The method 700 includes monitoring a value of at least one parameter of the patient that is associated with at least one condition of metabolic syndrome, type 2 diabetes, and/or pancreatis (step 704). The at least one parameter of the patient may include any suitable medical parameter that is indicative of a condition of metabolic syndrome, type 2 diabetes, and/or pancreatis. Such parameters may include one or more of blood pressure, glucose level, cholesterol level, diuresis, inflammation markers, insulin markers (e.g., C-peptide), and/or triglyceride level(s). One example an of inflammation marker that could be monitored includes Tumor Necrosis Factor (TNF¬α, TNF-alpha), a cytokine involved in systemic inflammation, which may be reduced by direct vagus nerve or tragus nerve stimulation. Another example of an inflammation marker is interleukin 6 (IL-6), a pro-inflammatory cytokine since stimulation of the atrial epicardial plexus may reduce the increase in IL-6 in the acute injury phase. Yet another example of an inflammation marker is interleukin 1 beta (IL-10), an inflammatory cytokine with receptors on the afferent vagus nerve—a potential modulation target. Still another example of an inflammatory marker includes interleukin 10 (IL-10), an anti-inflammatory cytokine that reduces the inflammatory effects of TNF¬α and IL-6.

Conditions of metabolic syndrome include high blood pressure, diabetes (e.g., type 2 diabetes), excess fat around the waist, and/or other conditions of metabolic syndrome that increase the risk of heart disease, stroke, and type 2 diabetes. Step 704 may monitor a single parameter of the patient or multiple parameters of the patient. As discussed in more detail below, the method 700 includes controlling a signal generator 616 based on a threshold value and the value of the at least one parameter being monitored. In accordance with example embodiments, one or more electrodes are coupled to the signal generator 616 to stimulate at least one spinal nerve (e.g., one or more DRGs) based on the electrical signal which causes a response by at least one anatomical element (e.g., the brain, liver, and/or pancreas) of the patient that changes the value of the at least one parameter of the patient (e.g., in a manner that helps treat a condition of metabolic syndrome).

As may be appreciated, a monitoring device 614 may provide data that enables monitoring the value of the at least one parameter. In one example, the data comprises the value or values of the parameter(s) being monitored (e.g., the monitoring device 614 itself is capable of determining the patient's blood glucose level). In another example, a device, such as processor 604, processes the data from the monitoring device 614 to determine the value or values of the parameter(s) being monitored (e.g., the monitoring device 614 passes raw data to the processor 604 that enables the processor 604 to determine the patient's blood glucose level). The data that enables parameter monitoring may be provided by the monitoring device 614 to the processor 604 continuously at regular or irregular intervals (e.g., every second, every 10 minutes, at particular times of the day or night, etc.). In one embodiment, the processor 604 may query the monitoring device 614 for the data. The query for data may be sent upon expiration of a timer that is tracking one or more aspects of a treatment, such as treatment duration (e.g., the processor 604 may query the monitoring device 614 upon expiration of the first and/or second durations of time discussed below).

The method 700 includes determining whether the value or values being monitored in step 704 are greater than respective threshold values (step 708). Each parameter being monitored may have an associated threshold value that is used to determine whether to activate or not activate the signal generator 616. For example, a threshold of 7 mmol/L may be implemented when the parameter being monitored includes blood glucose. Other thresholds may include a cholesterol level threshold value if monitoring cholesterol (e.g., a threshold of 5.0 mmol/L), a low-density lipoproteins (LDL) threshold value (e.g., a threshold of 3.5 mmol/L), triglyceride level threshold values if monitoring triglyceride levels (e.g., a threshold of 150 mg/dL), a blood pressure threshold value if monitoring blood pressure (e.g., a threshold of 140/100 mmHg), a threshold associated with an amount of body fluid (e.g., an impedance deviating more than 5% from normal within a week, assuming weight increase of 2.5 kg for someone of 50 kg), and/or the like.

If the value or values of the parameter or parameters being monitored do not exceed a respective threshold value, then the method 700 returns to step 704 to continue monitoring the parameter(s) of the patient. On the other hand, if the value or values of the parameter or parameters being monitored exceed a respective threshold value, then the method 700 includes controlling the signal generator 616 to generate the electrical signal (step 712). For example, when the patient's blood glucose level exceeds 7 mmol/L, then step 712 is carried out. In one example, the signal generator 616 is controlled to generate the electrical signal as a square wave with a frequency of 15 hz, a pulse width of 150 microseconds, and an initial current of 0.1 mA.

After step 712, the method 700 includes determining whether the value or values of parameters being monitored in step 704 are greater than their respective threshold values (step 716). The threshold value or values may be the same values used in step 708. If the respective threshold value or values are exceeded, the method 700 returns to step 712 and continues to generate the electrical signal. If the respective threshold value or values for the monitored parameter(s) is/are not exceeded, the method 700 includes controlling the signal generator 616 to cease generating the electrical signal (step 720). For example, when the patient's blood glucose level drops below 7 mmol/L, the signal generator 616 stops generating the electrical signal. Step 716 may be performed in conjunction with receiving the data from monitoring device 614. For example, step 716 may be performed each time data regarding the monitored parameter is received from the monitoring device 614.

In at least one embodiment, the method 700 includes iterating through steps 712 and 716 while adjusting at least one characteristic or signal parameter of the electrical signal in each iteration until the value(s) of the monitored parameter(s) drops below a respective threshold value. For example, the method 700 controls the signal generator 616 to output the electrical signal with incremented current values and/or adjusted pulse widths until the monitored parameter drops below the threshold value. By way of explanation, a first iteration of step 712 may include controlling the signal generator 616 to generate the electrical signal having a first current value for a first duration of time. Upon expiration of the first duration of time and when the value of the at least one parameter still exceeds the threshold value in step 716, the method 700 may iterate through step 712 again and control the signal generator 616 to generate the electrical signal having at least one adjusted characteristic compared to the previous iteration of step 712. For example, a second iteration of step 712 may include controlling the signal generator 616 to generate the electrical signal with a second current value larger than the first current value for a second duration of time. In at least one example embodiment, the current of the electrical signal is increased by 0.05 mA (starting with an initial current of 0.1 mA) for each iteration through step 712 until a maximum current is reached. In another embodiment, the current may be increased by different degrees for each iteration. For example, the amount of current increase may rise or fall for each subsequent iteration through step 712. For example, the current may be increased from an initial value by 0.25 mA, then increased by 0.5 mA, then increased by 0.75 mA, and so on for subsequent iterations until reaching the maximum current. The maximum current may be a current that is below a level that is known to stimulate the patient's ventral root (accidental stimulation of the ventral root may induce side effects for the patient). In another example, the current may be increased from an initial value by 0.75 mA, then increased by 0.5 mA, then increased by 0.25 mA, and so on for subsequent iterations until reaching the maximum current. As may be appreciated, the same approach as described above for current may be taken for adjusting pulse width of pulses of the electrical signal (e.g., a gradual increase or decrease in pulse width for each iteration of step 712).

Here, it should be understood that the determination in step 716 may depend on the type of parameter(s) being monitored. For example, although FIG. 7 is described with respect to keeping a value of a monitored parameter below an upper limit threshold value, the determination in step 716 may additionally or alternatively determine whether the value(s) of the monitored parameter(s) drops below a lower limit threshold value, and then generate the electrical signal in an iteration of step 712 in a manner that keeps the monitored parameter above the lower limit threshold value (and, in some cases, also below the parameter's upper limit threshold value). Keeping a monitored parameter above a lower limit threshold value may prevent potentially dangerous conditions from occurring, such as hypoglycemia (in the case of exceedingly low blood glucose levels), hypotension (in the case of exceedingly low blood pressure), and/or the like.

Other characteristics or signal parameters of the electrical signal that may be adjusted in each iteration of step 712 besides or in addition to current and/or pulse width include frequency, voltage, duty cycle, pulse type (e.g., square wave, sine wave, triangle wave), and/or the like.

As noted above, each iteration of step 712 may be carried out for a duration of time, where the duration of time is the same or different for some or all iterations. In at least one embodiment, each iteration of step 712 may be carried out for a shorter duration than the immediately preceding iteration, which may result in faster treatment of the condition of metabolic syndrome such as a high blood glucose level because higher current levels are implemented more quickly. For a treatment session having a total duration of 2.5 hours, a first iteration of step 712 may be carried out for one hour, a second iteration for 45 minutes, a third iteration for 30 minutes, and a fourth iteration for 15 minutes, with the electrical signal in each iteration increasing in current by 0.5 mA per iteration. If a treatment session ends (or some other prescribed amount of time passes) and the monitored parameter(s) of the patient are still above respective threshold values, then the processor 604 may issue an audio and/or visual alarm to, for example, the patient's mobile phone or other device (e.g., user interface 610) that is capable of producing the alarm in a manner that alerts an interested party to a potential health issue of the patient that needs further attention from a medical professional or to a device malfunction (e.g., a malfunction of the monitoring device 614 and/or the stimulating/blocking system 612).

In accordance with example embodiments, the electrical signal generated in step 712 may be received by one or more stimulating electrodes 400 that stimulate one or more DRGs at one or more of thoracic levels T7, T8, T9, T10, T11, and/or T12 which causes feedback in the patient's brain that limits food intake, inhibits sympathetic drive (e.g., inhibits sympathetic nerves), and/or promotes vagal stimulation, which in turn causes the pancreas to respond by increasing insulating production and/or that causes the liver to promote glycogenesis and/or to store more glucose in muscle tissue. In addition, the kidney's response to inhibition of sympathetic activation may lead to an increase in urinary excretion and decrease in sodium resorption.

Although not explicitly illustrated, it should be appreciated that the signal generator 616 may be controlled to stop generating the electrical signal in response to other triggers, such as in response to a maximum amount of time lapsing since beginning treatment and/or in response to instructions from patient or medical professional (e.g., provided to the system 600 through a mobile phone or other suitable device when, for example, the patient is experiencing negative side effects).

The method 700 may implement a feedback mechanism that enables the optimization of various parameters involved in the method 700 with the goal of obtaining desired patient outcomes as fast as possible. To this end, the method 700 may include storing and/or adjusting optimization data in memory 606 to improve future treatments (step 724). Such optimization data may include data for electrical signal optimization data 620. In at least one example, the processor

604 may correlate aspects of one or more iterations of step 712 during the treatment session with aspects of the patient outcome to train the system to improve subsequent treatment sessions. For example, data may be stored and/or adjusted to correlate the effect of each iteration of step 712 on the monitored parameter with the duration of each iteration of step 712, the characteristics of the electrical signal in each iteration of step 712, and/or the like. Other data may be stored and/or adjusted at step 724, such as how often the monitoring device 714 provides data to the processor 604. The stored data may include a listing of patient side effects and when they occurred, which may be used to take action aimed at reducing side effects in future treatments.

Figure 8A:
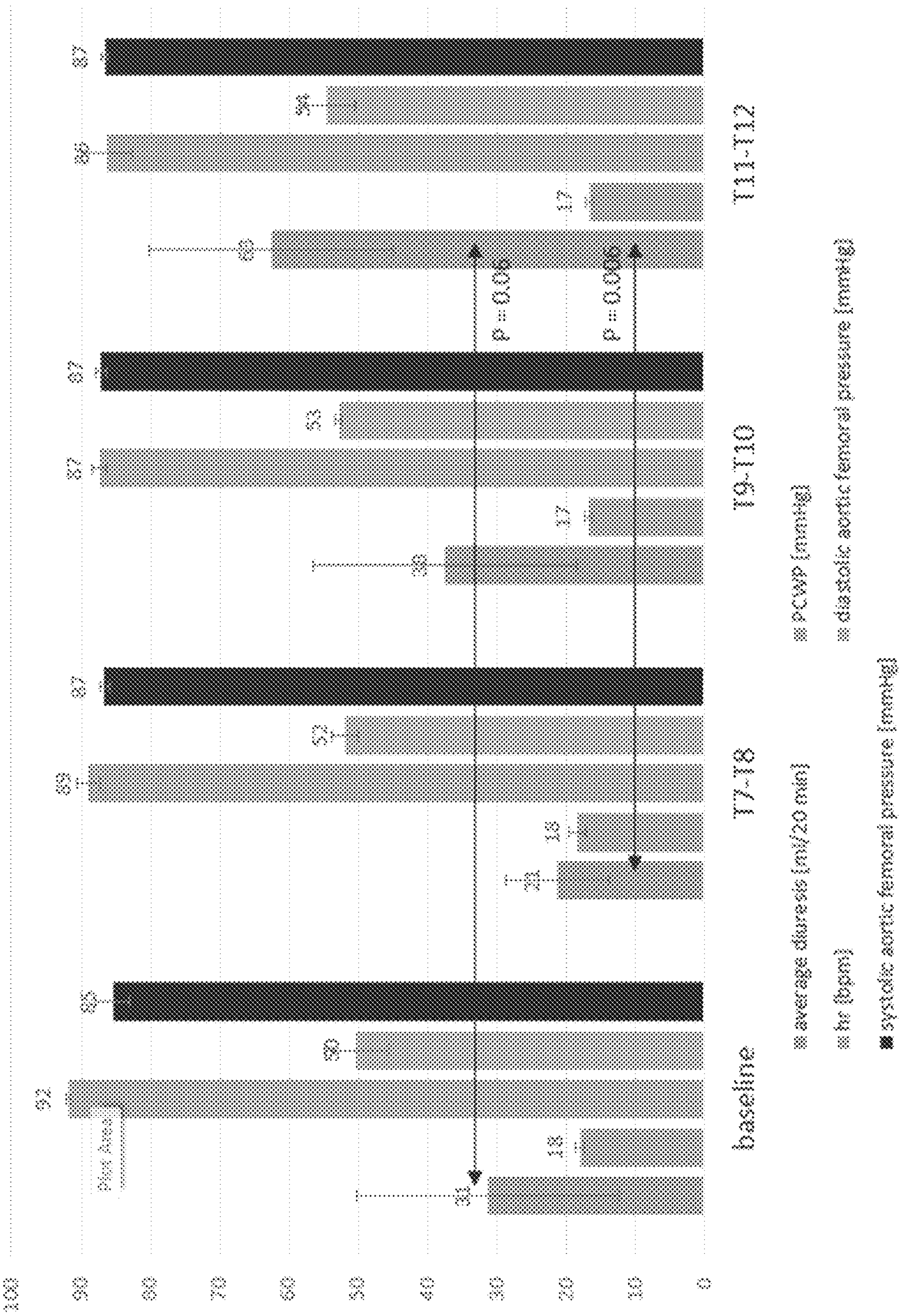
FIGS. 8A-9B show the results for stimulation experiments involving diuresis and C-peptide (insulin marker) measurements.
Figure 8B:
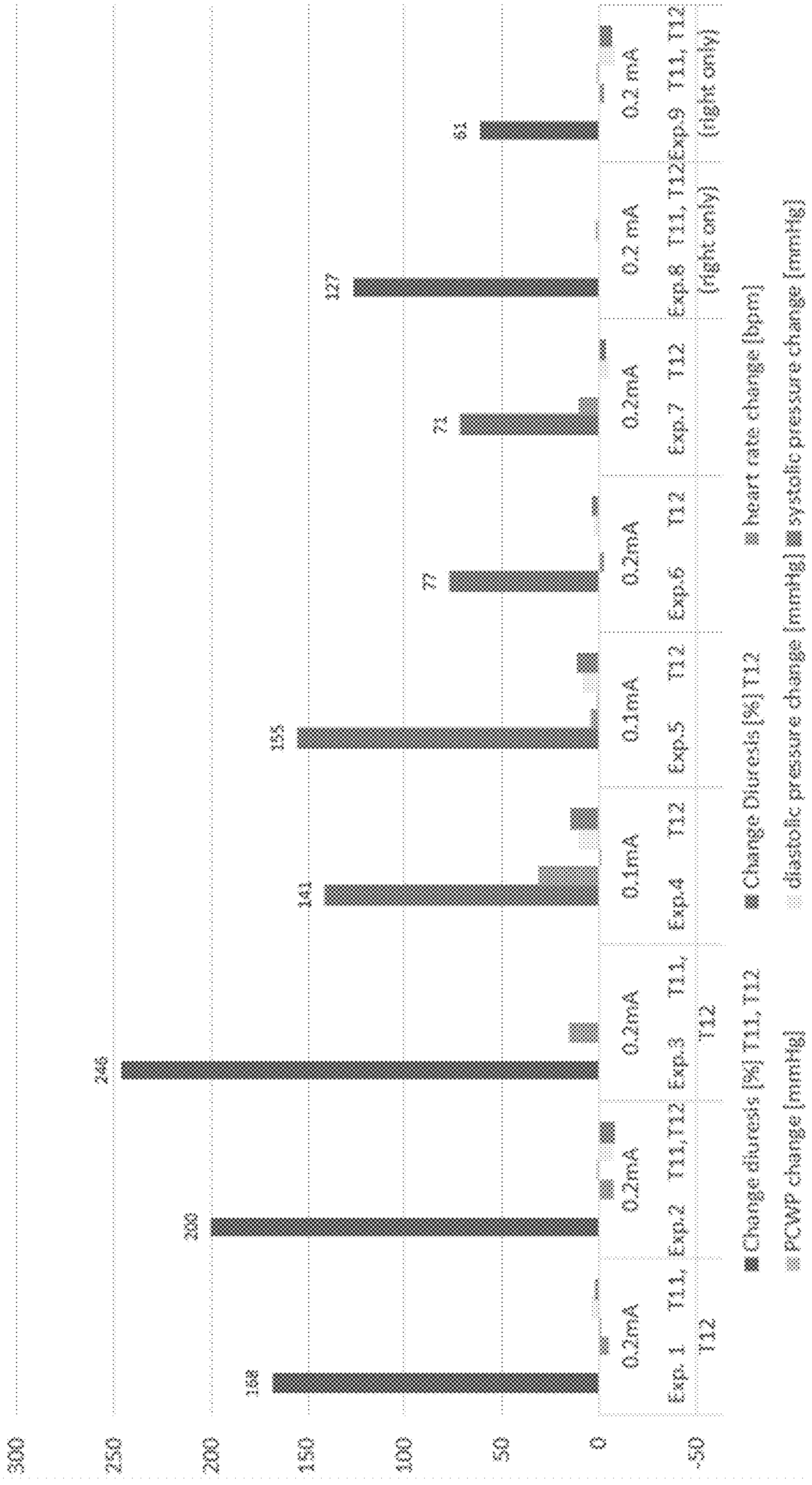
Figure 9A:
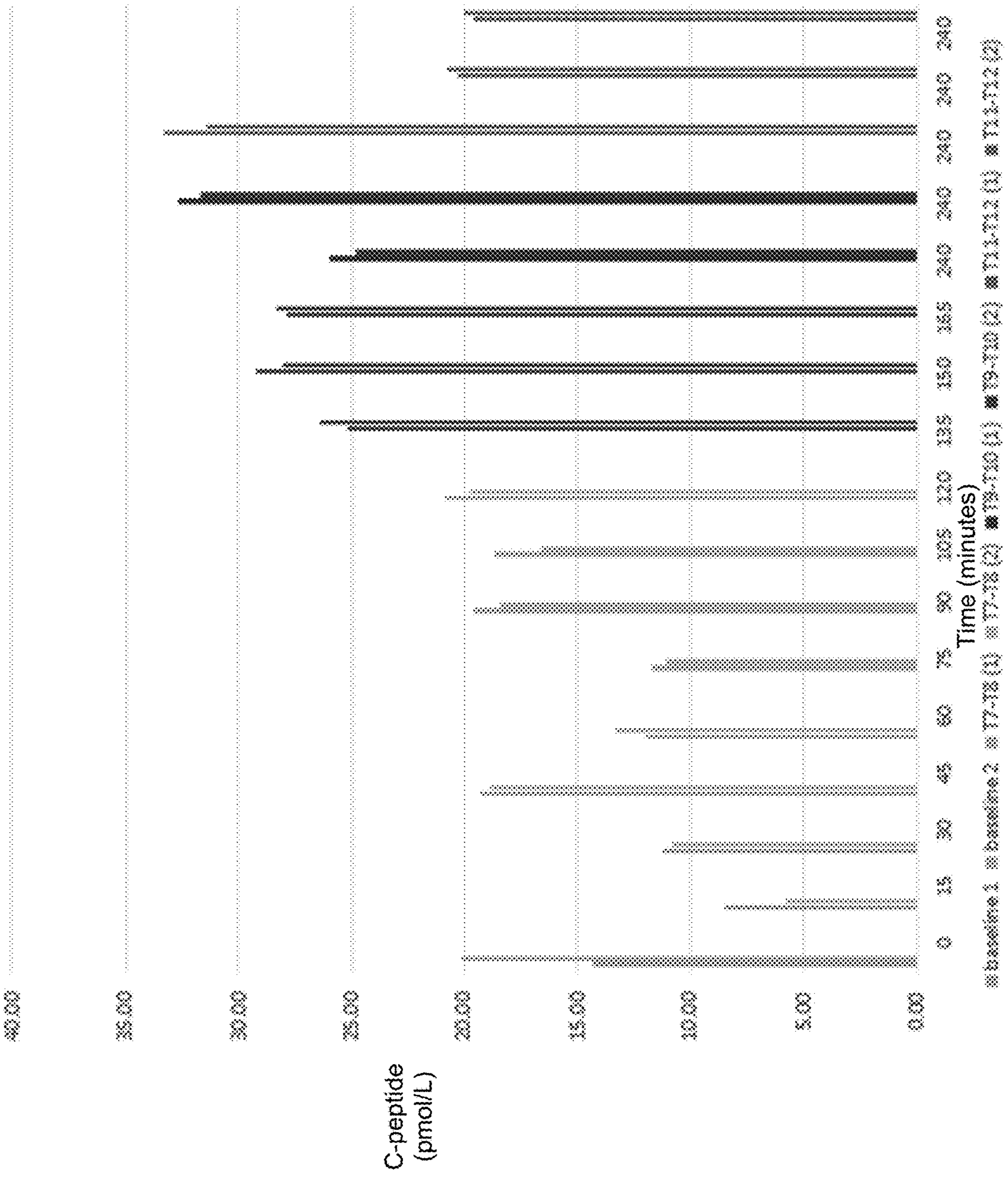
Figure 9B:
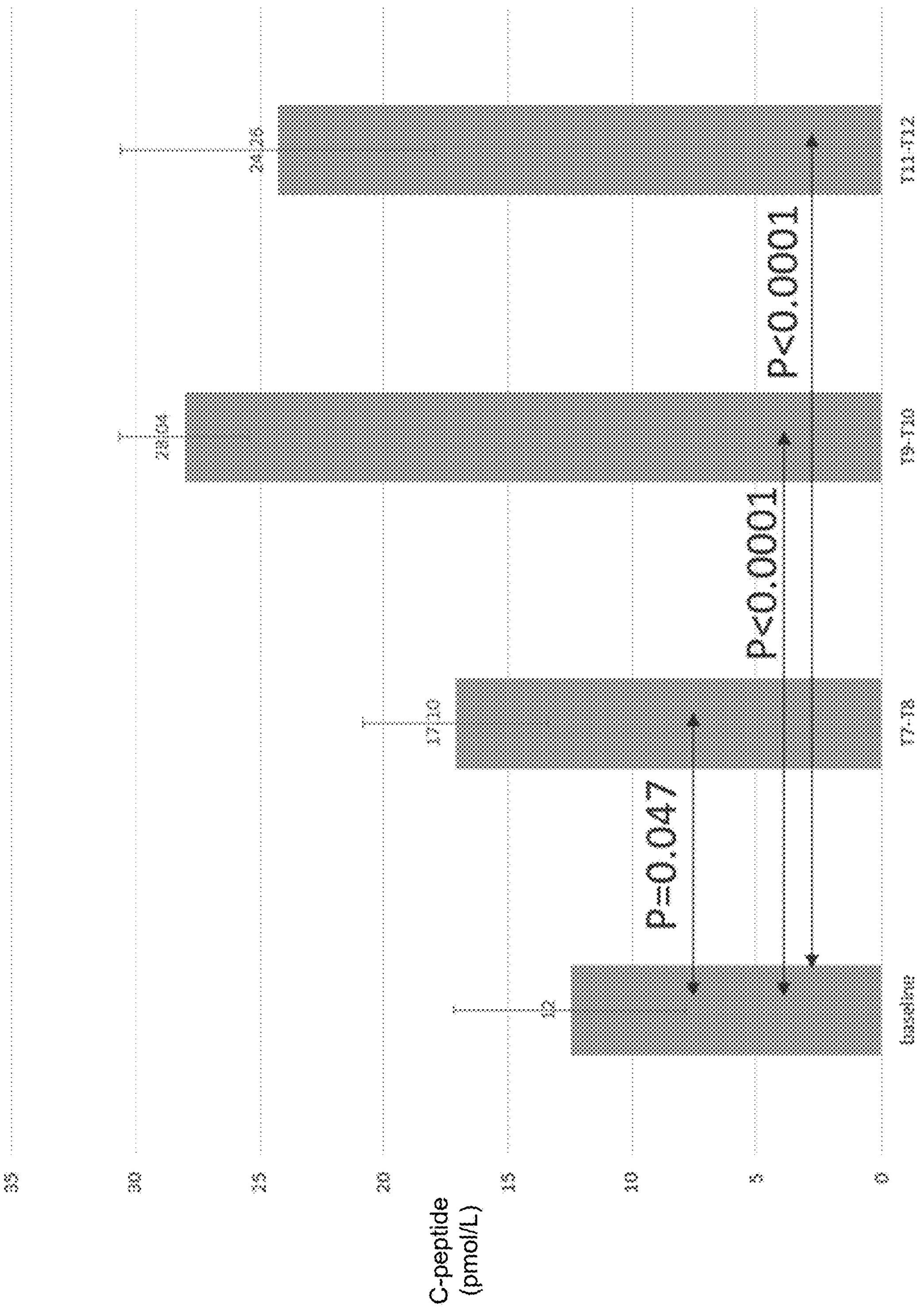

Example embodiments will now be described with reference to FIGS. 8A-9B which show various experimental results for spinal nerve stimulation to treat a condition of metabolic syndrome and/or diabetes type 2. More specifically, FIGS. 8A to 9B show results for experiments relating to a pig, with FIGS. 8A and 8B illustrating diuresis results, and with FIGS. 9A and 9B illustrating insulin marker measurements (C-peptide measurements). The units of each axis in the figures are shown on the axes themselves or in the legend below the figure (in which case the y-axis is typically unitless).

The experiments were conducted with a pig being volume overloaded with an elevated and stable pulmonary capillary wedge pressure (PCWP) generated by infusion of isotonic fluid. Diuresis results were measured under conditions of stable high filling pressures and stable heart rates and measurements were taken when the animals were stable also in terms of glucose levels. Each experiment involved a one hour baseline measurement followed by measurements during stimulation. In FIGS. 8A and 9A, stimulation took place for one hour bilaterally at thoracic levels T7 and T8, for subsequently one hour at thoracic levels T9 and T10, and for subsequently one hour at thoracic levels T11 and T12. The experiments conducted in FIGS. 8A and 9A provided substantially constant stimulation at each T-level with an electrical signal having a current of 0.2 mA, a frequency of 15 Hz, and a pulse width of 150 microseconds. In general, multiple measurements were taken per hour (e.g., four measurements per hour) for each parameter of interest (diuresis, C-peptide, and lipids—not shown here) and for other parameters such as blood pressure, heart rate, central venous pressure, and PCWP. Given the three different levels of stimulation with two leads at each level, six leads were used (e.g., like leads 108 in FIG. 4B).

FIG. 8A illustrates a bar graph of certain measurements, including average diuresis measurements, with standard distributions and P values. FIG. 8B illustrates a bar graph of nine experiments to show percentage change in diuresis when stimulating levels T11 and T12 with a constant current of 0.1 mA or 0.2 mA for a specified duration (e.g., 1 hour), a pulse width of 150 microseconds, and frequency of 15 Hz. As shown, the percentage increase in diuresis ranges from 61% to 246% when stimulating versus no stimulation. It was found via autopsy that the left lead was not positioned correctly in experiments 8 and 9, and thus, these experiments indicate "right only." FIG. 9A shows two peptide measurements from two different samples of the same animal at each time point. FIG. 9B illustrates a bar graph showing the averages of C-peptide measurements taken in FIG. 9A with standard distributions and probability values P. As may be appreciated, the P values in each figure indicate that there is a strong likelihood that the illustrated effects on diuresis and C-peptide measurements are due to the electrical stimulation provided to the T levels in the experiments.

As may be appreciated from FIGS. 8A to 9B, electrical stimulation at levels T7 to T12 resulted in an increase of diuresis and an increase in C-peptide levels which are indicative of increased insulin production (e.g., at T7/T8 stimulation, at T9/T10 stimulation, and at T11/T12 stimulation). Although not explicitly shown in these results, the electrical stimulation may also result in an overall decrease in cholesterol and triglycerides.

At least one embodiment of the present disclosure relates to electrode selection and/or optimization for a lead 108. With respect to a paddle lead, for example, it may be useful to identify which electrodes are optimal for stimulation and which electrodes should be used for sensing. Compound action potentials (CAPs) of nerve fibers may be utilized for such a selection/optimization process. Different nerve fibers have different conduction velocities, and the different conduction velocities may provide information about the activated nerve. For example, sensory fibers may be distinguished from motor fibers due to each type of fiber having a different conduction velocity. In addition, different nerve fibers may produce different CAPs. For example, a type of nerve fiber may be known to generate a certain number of CAP pulses and/or CAP pulses with distinct shape(s). At least one embodiment of the present disclosure relates to a technique for optimization of the electrode configuration and stimulation parameters using at least one electrode on a lead 108 as a sensing electrode to select which electrodes 108 should be stimulation electrodes by optimizing certain parameters, such as conduction velocity and sensed stimulation output (e.g., CAP amplitude). This technique is accomplished algorithmically by using a matrix of values for each electrode on the lead 108. For a paddle lead 108, the algorithm may adhere to the following pseudocode:

```
For each paddle_lead (1 to x)
  For each electrode (1 to n)
    y(ii) = function measure_conduction_velocity( );
    z(ii) = function_measure_CAP_amplitude( )
  End for each electrode
End (for each paddle_lead)
Function find_maximum (y, z)
```

In the pseudocode above, n is the number of electrode elements on each paddle electrode (the number of electrodes on each paddle may be equal), x is the number of paddles or other leads, (e.g., three paddle leads), y is the measured conduction velocity in a vectorized format (e.g., an array of values that is based on time taken for a pulse to travel between two electrodes), and z is the measured CAP amplitude in a vectorized format (e.g., an average amplitude of a set of CAP pulses). The function find_maximum is an optimization routine to find the index of the greatest stimulation parameters. Stated another way, the goal of the above algorithm is to find the electrode(s) that maximize conduction velocity and maximize CAP amplitude.

The electrical model of the spinal cord and the volume conduction of certain elements as well as electrical behaviors of neurons and fibers enable prediction of recruitment using CAPs. The electrodes with the best recruitment parameters mean the electrodes are stimulating sensory fibers and not motor fibers. In at least one embodiment, an electrode associated with the highest conduction velocity and CAP amplitude is selected as the stimulation electrode. In some examples, multiple electrodes are selected as stimulation electrodes in which case the selected electrodes are associated with higher conduction velocities and CAP amplitudes than remaining electrodes.

In some examples, an electrode combination with highest effect/side effect ratio is selected. In some examples, electrode selection is accomplished with a self-learning or machine learning algorithm. In any event, one or more of the unselected electrodes on a lead 108 (i.e., non-stimulating electrodes) may be used as sensing electrodes during stimulation. In at least one embodiment, the stimulation current of the stimulation electrode(s) is in the range of 0.1 mA-0.4 mA since higher currents may result in accidental stimulation of the ventral roots, which leads to motor stimulation that may have undesired effects (e.g., an opposite effect compared to stimulation of the dorsal root ganglion sensory fibers).

In some examples, electrode selection depends upon or is based on the position of the patient, with different electrodes being selected for stimulation depending on whether the patient is in a sitting position, standing position, or prone position. In this case, the device 104 may include an accelerometer that senses the position of the patient, which enables the device 104 to be programmed to select different groups of electrodes depending on patient position. For example, the device 104 may select sitting group electrodes A, standing group electrodes B, or laying group electrodes C. Selecting stimulating electrodes based on patient position accounts for how the electrodes may be differently situated or oriented in relation to the DRG in the different patient positions, which may alter stimulation parameters of the electrical signal (current, pulse width, duty cycle, and/or frequency) to achieve a desired effect. For example, each group of electrodes A, B, C may have a first set of stimulation parameters A1, B1, C1 for a basal rate test and may have a second set of stimulation parameters A2, B2, C2 for extra bolus after ingesting food. For instance, if the patient is determined to be sitting and to have recently ingested food, then group A electrodes are selected as stimulating electrodes to stimulate with stimulation parameters A2. Meanwhile, if the patient is determined to be standing and to have requested or require a basal rate test, then group B electrodes are selected as stimulating electrodes to stimulate with stimulation parameters B2. Selection of a group of stimulating electrodes may be programmed and/or patient activated and combined with activity sensed by the accelerometer to create different stimulation parameters for each group of stimulating electrodes.

As described with reference to FIG. 7, at least one embodiment relates to a closed loop system meant to keep a patient's levels within a normal range (e.g., between 90 mg/dL and 120 mg/dL for glucose). In some examples and as discussed in more detail below, a monitoring method similar or the same as that described with reference to FIG. 7 may be further adjusted to account for food intake, exercise, and/or other activity that may vary levels of a monitored parameter relevant to metabolic syndrome and/or type 2 diabetes (e.g., glucose levels and lipid levels such as cholesterol or triglyceride levels). For example, if the glucose readings are out of range for a specified period of time (e.g., 10 minutes) or if there is a sudden change in slew rate (meaning glucose levels are shifting rapidly), then the stimulation system may be turned on until the slew rate stabilizes or the systemic glucose levels are within range for a specified period. In addition, a monitoring method according to at least one embodiment may have predictive capabilities so that the method that not only reacts to measured glucose shifts, but can also predict when glucose ranges will exceed acceptable limits based on food intake and/or exercise. This predictive method may take various factors such as anticipated patient food intake (e.g., based on patient proximity to a restaurant frequented by the patient), actual patient food intake (e.g., carbohydrate intake as manually entered into the system by the patient, for example, via an app on a phone), anticipated exercise (e.g., based on proximity to an exercise facility frequented by the patient), actual patient exercise (e.g., as entered manually by the patient just before exercise), anticipated use of a drug, actual use of a drug (e.g., as entered manually by the patient upon use or just before use), anticipated use of insulin, and/or actual use insulin (e.g., as entered manually by the patient upon use or just before use). The same concepts described above for glucose monitoring may be applied to lipid monitoring to monitor and adjust lipid levels. Lipid levels can be either measured manually or through a monitoring device.

Figure 10:
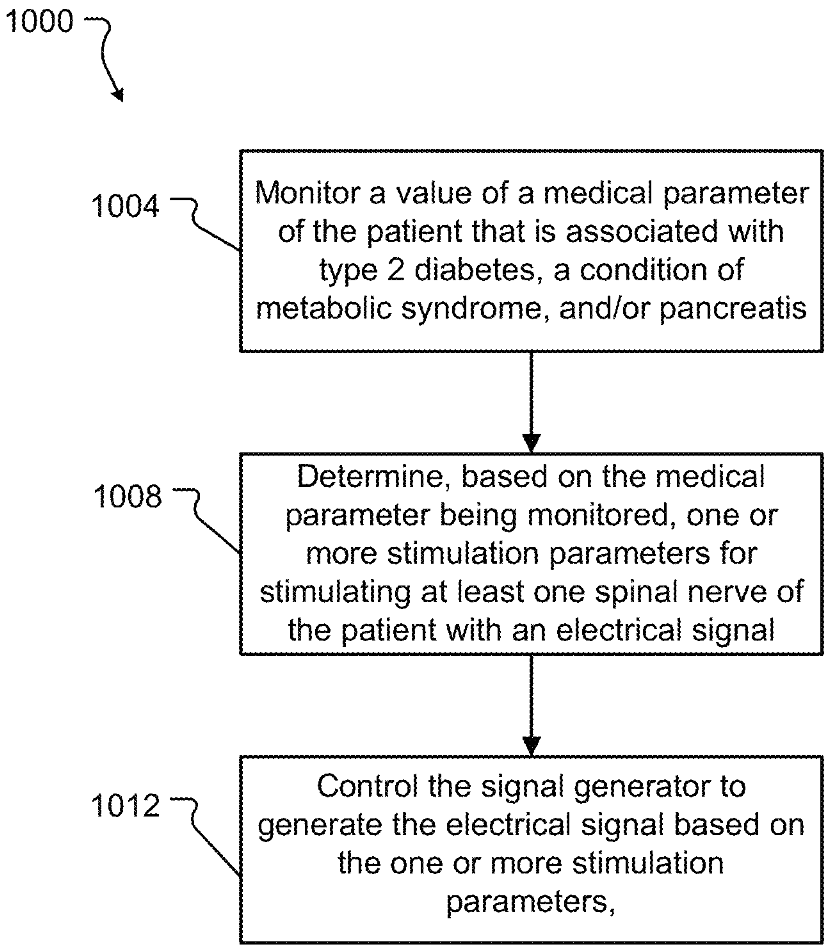
FIG. 10 is a flowchart according to at least one embodiment of the present disclosure.

FIG. 10 depicts a method 1000 that may be used, for example, to perform neuromodulation techniques (e.g., stimulation therapy) to treat diabetes type 2, at least one condition of metabolic syndrome, and/or pancreatis for a patient. The method 1000 (and/or one or more steps thereof) may be carried out or otherwise performed, for example, by at least one processor. The at least one processor may be the same as or similar to the processor 604 or the processor(s) of the device 104 or 204 described above. The at least one processor may be part of the device 104 or 204 (such as an implantable pulse generator) or part of a control unit in communication with the device 104 or 204. A processor other than any processor described herein may also be used to execute the method 1000. The at least one processor may perform the method 1000 by executing elements stored in a memory (such as a memory 606 in the device 104 as described above). The elements stored in the memory and executed by the processor may cause the processor to execute one or more steps of a function as shown in method 1000. One or more portions of a method 1000 may be performed by the processor executing any of the contents of memory, such as providing stimulation to a nerve with an electrical signal, executing an electrical signal optimization such as the electrical signal optimization 620, and/or any associated operations as described herein.

The method 1000 includes monitoring a value of a medical parameter of the patient that is associated with type 2 diabetes, a condition of metabolic syndrome, pancreatis, or any combination thereof (step 1004). The medical parameter being monitored may comprise a blood glucose level of the patient, an inflammatory marker (e.g., IL-6, TNF¬α, TNF-alpha, IL-1β, and/or IL-10), and/or a lipid level of the patient. Step 1004 may be performed in the same or similar manner as step 704. The medical parameter may be monitored by a monitoring device 614 and/or may be manually entered into a user interface (e.g., an app on a smartphone) by the patient or caretaker.

The method 1000 includes determining one or more stimulation parameters for stimulating at least one spinal nerve of the patient with an electrical signal (step 1008). As noted herein, the electrical signal is introduced to at least one spinal nerve (e.g., a DRG at one or more of thoracic levels T7 thru T12 of the patient) by one or more electrodes implanted near the spinal nerve, which causes a response by at least one anatomical element of the patient that changes the value of the medical parameter for the patient. The one or more stimulation parameters determined in step 1008 may include values for characteristics of the electrical signal applied to one or more stimulation electrodes, such as values for current, pulse width, duty cycle, and/or frequency of the electrical signal, type of waveform for the electrical signal (square, sine, triangle), and/or duration of stimulation. As may be appreciated, step 1008 may be performed on-the-fly, for example, in response to detecting that the medical parameter being monitored needs to adjusted. In this case, step 1008 may take various patient-related factors into account, such as age, gender, condition being treated, height, weight, rate of change in the monitored medical parameter, etc., and determine the one or more stimulation parameters in real time based these factors. Additionally or alternatively, step 1008 comprises selecting the one or more stimulation parameters from a preexisting list of stimulation parameters known to be effective for adjusting the monitored medical parameter in a desired manner. The same patient-related factors mentioned above may be considered for such a selection. In some examples, step 1008 includes a selection of stimulation electrodes in accordance with the electrode selection/optimization process described herein.

In any event, the stimulation parameters and/or stimulating electrodes determined in step 1008 may be different depending on the condition being treated. For example, one set of stimulation parameters may be selected for treating type two diabetes while another, different set, of stimulation parameters may be selected for treating a condition of metabolic syndrome. The stimulation parameters and/or stimulating electrodes determined or selected in step 1008 may also depend on the patient. For instance, as described in more detail below with reference to FIG. 11, the selected stimulation parameters and/or stimulation electrodes may be known from earlier testing to not cause side effects in the patient such as tingling, discomfort, and increased heart rate. Some patients may experience side effects and some patients may not with the same set of stimulation electrodes and parameters, and thus, the selection in step 1008 may be tailored to the specific patient.

Additionally or alternatively, step 1008 is performed based on additional information. For example, as described herein, the one or more stimulation parameters may be selected or determined based on activity information about activity of the patient that is known to affect the value of the medical parameter. The activity information may include information about past patient activity, current patient activity, predicted patient activity, or any combination thereof. In some examples, the past patient activity includes patient intake of food or patient intake of a drug, the current patient activity includes current patient exercise, and the predicted patient activity includes predicted patient exercise and predicted patient intake of food or predicted patient intake of a drug. In at least one embodiment, step 1008 selects the one or more electrodes, from a larger group of electrodes (i.e., electrodes on the lead 108), as stimulation electrodes based on compound action potentials (CAPs). For example, the one or more electrodes are selected as stimulation electrodes based on measurements of CAP conduction velocity and CAP signal amplitude. The measurements of CAP conduction velocity and CAP signal amplitude may be vectorized measurements. In at least one embodiment, the one or more electrodes are selected based on a detected patient position.

As may be appreciated, stimulation parameters and electrodes are selected with the goal of activating the correct nerve fibers at a spinal level and for a time period that maximizes efficacy without inducing intolerable side effects.

The method 1000 further comprises controlling the signal generator 616 to generate the electrical signal based on the one or more stimulation parameters (step 1012). For example, step 1012 generates the electrical signal to have the values for current, duty cycle, frequency, and/or pulse width determined in step 1012. The signal generator 616 may be controlled to generate the electrical signal when the value of the medical parameter is not within an acceptable range of values, and to cease generating the electrical signal when the value of the medical parameter is within the acceptable range of values or when the value of the medical parameter falls below a lower limit threshold value. In some examples, step 1012 controls the signal generator 616 to generate the electrical signal in a manner that keeps the value of the medical parameter within an acceptable range of values.

Figure 11:
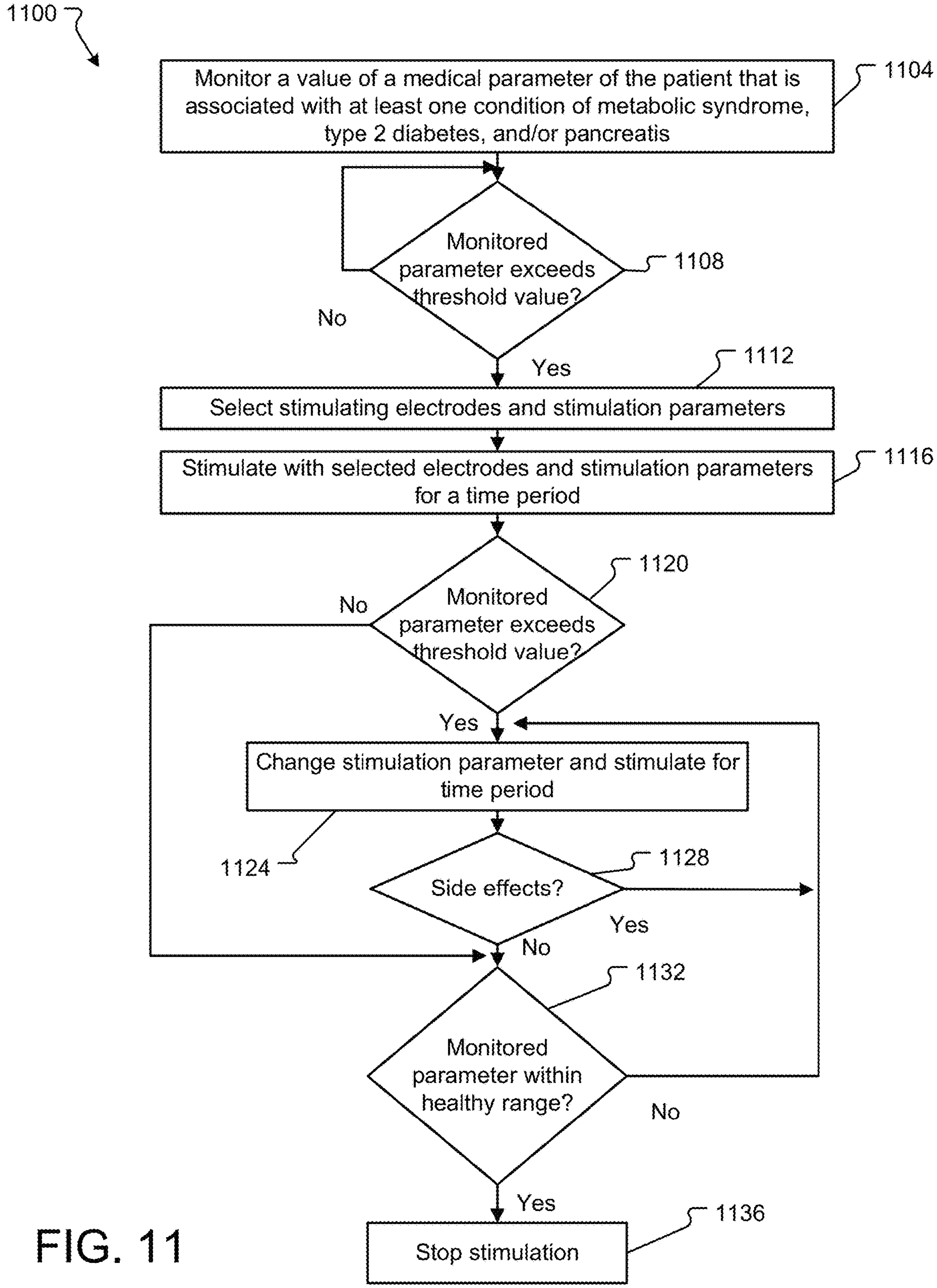
FIG. 11 is a flowchart according to at least one embodiment of the present disclosure.

FIG. 11 depicts a method 1100 that may be used, for example, to perform neuromodulation techniques (e.g., stimulation therapy) to treat diabetes type 2, at least one condition of metabolic syndrome, and/or pancreatis for a patient. The method 1100 (and/or one or more steps thereof) may be carried out or otherwise performed, for example, by at least one processor. The at least one processor may be the same as or similar to the processor 604 or the processor(s) of the device 104 or 204 described above. The at least one processor may be part of the device 104 or 204 (such as an implantable pulse generator) or part of a control unit in communication with the device 104 or 204. A processor other than any processor described herein may also be used to execute the method 1100. The at least one processor may perform the method 1100 by executing elements stored in a memory (such as a memory 606 in the device 104 as described above). The elements stored in the memory and executed by the processor may cause the processor to execute one or more steps of a function as shown in method 1100. One or more portions of a method 1100 may be performed by the processor executing any of the contents of memory, such as providing stimulation to a nerve with an electrical signal, executing an electrical signal optimization such as the electrical signal optimization 620, and/or any associated operations as described herein.

The method 1100 may be considered as an example implementation of or a more detailed version of the methods 700 and/or 1000. The method 1100 includes monitoring a value of a medical parameter (also referred to as "parameter" herein) of the patient that is associated with at least one condition of metabolic syndrome, type 2 diabetes, and/or pancreatis (step 1104). Step 1104 may be performed in the same or similar manner as steps 704 and/or 1004. In some examples, the monitored parameter may be a blood glucose level of the patient, an inflammatory marker (e.g., IL-6, TNF¬α, TNF-alpha, IL-1β, and/or IL-10), one or more lipid levels of the patient (e.g., cholesterol, LDL, triglycerides), or any combination thereof.

The method 1100 includes determining whether the monitored parameter in step 1104 exceeds a threshold value (step 1108). If not, step 1108 repeats and continues to check whether the threshold value is exceeded. When the threshold value is exceeded, the method 1100 selects stimulation parameters and, in some cases, stimulating electrodes (step 1112). In some cases, step 1108 determines whether the threshold value is exceeded for an extended time, such as 10 minutes when monitoring blood glucose or one day when monitoring lipid levels, or other prescribed period of time. As may be appreciated, the threshold value is generally a value that represents an upper limit of the parameter being monitored (e.g., 120 mg/dL for blood glucose, 5.0 mmol/L for cholesterol, 3.5 mmol/L for LDL, 150 mg/dL for triglycerides). In some examples, step 1112 comprises determining whether a rate of change of the monitored parameter exceeds a threshold rate since the rate of change can be used as a trigger to begin stimulation. Step 1112 may include selecting stimulating electrodes for stimulating a spinal nerve (e.g., a DRG at one of T7 thru T12 thoracic levels) with an electrical signal and/or selecting stimulation parameters for the electrical signal in accordance with the selection processes described herein. In any event, the selections made in step

1112 may be known to avoid stimulation side effects such as tingling, discomfort, and increased heart rate. In one specific, non-limiting example, the stimulation parameters are a current of 0.1 mA, 150 microsecond pulse width, and a frequency of 15 Hz. As may be appreciated, step 1108 may be performed throughout all or some portion of the stimulation time period. In some examples, step 1108 is performed at regular intervals, for example, every 15 minutes or every few hours depending on the parameter being monitored.

Thereafter, the method 1100 includes stimulating the spinal nerve with the selected stimulation parameters and the selected electrodes for a period of time (step 1116). The period of time may depend on the type of medical parameter being monitored and/or be selected as part of the stimulation parameters in step 1112. For example, if blood glucose is being monitored, then the period of time may be a matter of minutes (e.g., 10 minutes) to three hours. On the other hand, if a lipid level is monitored, then the period of time may be on the order of several hours (e.g., 12 hours) to multiple days (e.g., two or three days) because lipid levels are slower to respond to DRG stimulation.

Subsequent to step 1116, the method 1100 includes again determining whether the monitored parameter exceeds the threshold value from step 1108 (step 1120). If so, then the system deduces that the stimulation parameters selected in operation 1116 are not having the desired effect, and the method 1100 changes one or more of the stimulation parameters and continues stimulating for another time period (step 1124). If not, the method 1100 proceeds to check whether the value of the monitored parameter is within a healthy range of values (step 1132). As may be appreciated, step 1120 may be performed after the stimulation time period from step 1116 or throughout all or some portion of the stimulation time period. In some examples, step 1120 is performed at regular intervals, for example, every 15 minutes or every few hours depending on the parameter being monitored.

Step 1124 may change one or more of the stimulation parameters from the initial determination of the stimulation parameters in operation 1112. For example, step 1124 includes changing current of the electrical signal, changing pulse width of the electrical signal, changing duty cycle of the electrical signal, and/or changing frequency of the electrical signal. The stimulation parameters may be changed in a manner intended to affect the medical parameter being monitored in a desired manner (e.g., to raise or lower the value of the medical parameter). In one specific, non-limiting example where blood glucose or a lipid is being monitored, step 1124 increases current by 0.1 mA and increases pulse width by 15 microseconds with the notion that these increases will bring the blood glucose or lipid level down. In some cases, as discussed in more detail below, step 1124 changes one or more stimulation parameters with the goal of reducing one or more side effects. The patient may be notified of the change in stimulation parameter(s) and/or be prompted to authorize any changes made in step 1124 through a mobile app on the patient's phone. Step 1124 may be carried out in a manner that ensures stimulation parameters do not exceed upper and/or lower limit values. For example, current of the electrical signal may be capped at a value of 0.4 mA, and thus, any changes made to current at step 1124 should ensure that the current of the electrical signal stays at or below 0.4 mA.

The method 1100 includes determining whether the patient is experiencing side effects from the stimulation parameter(s) changed in step 1124 (step 1128) since increasing the current of the electrical signal providing stimulation in step 1124 may cause the patient to experience tingling or other side effects. Step 1128 may occur at any point after changing the stimulation parameter in step 1124. For example, shortly after changing the stimulation parameter(s) in step 112 (e.g., within 5 minutes), the patient may inform the system through the mobile app that a particular side effect is occurring. In some examples, the mobile app prompts the patient for input as to whether any side effects are being experienced after step 1124. If the system receives an indication that side effects are occurring, then the method 1100 may return to step 1124 to again adjust one or more stimulation parameters. In this iteration, however, step 1124 may change one or more stimulation parameters in a manner that is intended to reduce or eliminate the side effect(s) being experienced by the patient while maintaining effective stimulation. For example, in the above example given for step 1124 where current of the electrical signal was increased by 0.1 mA and pulse width of the electrical signal was increased by 15 microseconds after step 1120, the iteration of step 1124 may reduce the current by 0.05 mA and reduce the pulse width by 8 microseconds to see if the reductions diminish or eliminate the experienced side effect(s). The amount of adjustment made to stimulation parameters in step 1124 when side effects are being experienced may be predetermined or may be determined in real time. In some examples, adjustments made to stimulation parameters in step 1124 in response to the patient experiencing side effects are done in a step-wise fashion, such as a 25% reduction in values of stimulation parameters compared to the initial change made in step 1124 after step 1120. In at least one embodiment, the step adjustments made to stimulation parameters are gradually larger for each iteration through step 1124 and 1128 until the side effects are sufficiently reduced (e.g., a 5% reduction in current in the first iteration, a 15% reduction in current in the second iteration, a 25% reduction in current in the third iteration, and so on until the side effects are reduced or eliminated).

Subsequent to step 1128, the method 1100 includes determining whether the value of the monitored parameter is within a healthy or acceptable range of values for that parameter at that particular instant in time (step 1132). If so, the method 1100 proceeds to stop the stimulation (step 1136). If not, the method 1100 returns to step 1124. In practical terms, step 1132 decides whether the parameter being monitored has been brought to a level that is considered healthy or normal for the patient and, if so, the stimulation is stopped so as not to bring the value of the parameter to an unhealthy level (e.g., to prevent hypoglycemia in the case of blood glucose monitoring). Otherwise, the system deduces that further stimulation is needed and returns to step 1124 to again adjust one or stimulation parameters in a manner that is intended to bring the medical parameter being monitored into a healthy range.

Iterations of step 1124 that occur subsequent to step 1132 may adjust stimulation parameters not changed by iterations of step 1124 that occurred after step 1120 and/or 1128. For example, in the event that a first iteration of step 1124 increased current but not pulse width, then a second iteration of step 1124 performed after step 1132 may change pulse width and not current.

Here, it should be appreciated that the methods and systems described herein may also be applied to treat pancreatis and/or diabetes type 2 by stimulating spinal nerves (e.g., DRGs) that cause a response by a patient's pancreas. Stimulation of afferent fibers derived from the pancreas may affect the efferent fibers to the pancreas and in turn affect insulin production as well as inflammation markers. The pancreas produces insulin and glucagon, hormones which lower and raise blood glucose levels, respectively. The pancreas is innervated both vagally and sympathetically. The nerves contain afferent and efferent traffic information. The afferent sympathetic nerves traffic sensory information via the dorsal root ganglions. The dorsal root ganglions from the pancreas travel via the celiac ganglion, and the afferent nerves control metabolic homeostasis, inflammation, and pain. According to embodiments, pancreatic release of insulin can be increased by stimulating the dorsal root ganglions from T6-L2 through, for example, lateral epidural stimulation, which will lead to a decrease in blood glucose level.

In examples that stimulate nerves that affect the pancreas, the system 600 may be used to carryout one or more of the methods describe herein, such as the methods in FIGS. 7, 10, and 11 with the DRG(s) being stimulated at the T6, T7, T8, T9, T10, T11, T12, L1, and/or L2 levels of the patient's spine to cause a response by the patient's pancreas that produces insulin. As described herein, stimulation may occur at multiple spinal levels simultaneously. The medical parameter being monitored may be the same as the parameter(s) monitored in FIGS. 7, 10, and 11 (e.g., glucose). In some cases, the parameter being monitored comprises one or more inflammation markers associated with pancreatis, such as white blood cell count, IL-6, TNF¬α, TNF-alpha, IL-1β, IL-10, and/or C-reactive protein. In an example where the IL-6 marker level is monitored in a closed loop method for treating pancreatis, stimulation one or more of T6 to L2 levels may be triggered upon the IL-6 marker exceeding a threshold. Thereafter, the closed loop method continues to monitor the IL-6 marker (or other monitored marker) and make stimulation adjustments in the same or similar manner as that described with reference to FIGS. 7, 10, and/or 11 (e.g., change one or more stimulation parameters to optimize the desired effects while mitigating or avoiding side effects).

Some examples for affecting the pancreas include nerve blocking instead of or in addition to nerve stimulation. In this case, the stimulation signals described herein and with reference to FIGS. 7, 10, and 11 may be replaced with nerve blocking signals, such as electrical signals having a frequency in the range of 2 kHz to 20 kHz. In some cases, nerve blocking may be achieved with an electrical signal having a modified sinusoidal waveform and an ultra-low frequency, such as a frequency below 2 Hz. The same or similar methods described above with reference to FIGS. 7, 10, and 11 may be applied to nerve blocking in that various parameters of the electrical signal for nerve blocking may be adjusted in the same manner the stimulation parameters of the signal for stimulation.

It should be appreciated that example embodiments have shown and described with reference to specific values for various parameters (e.g., threshold values, electrical signal characteristics, durations of iterations for steps, etc.), but that these values may vary or be adjusted based on empirical evidence and/or design preference.

The present disclosure encompasses embodiments of the methods described herein that comprise more or fewer steps than those described above, and/or one or more steps that are different than the steps described above.

As noted above, the present disclosure encompasses methods with fewer than all of the steps identified in the figures (and the corresponding description of the methods), as well as methods that include additional steps beyond those identified in the figures (and the corresponding description of the methods). The present disclosure also encompasses methods that comprise one or more steps from one method described herein, and one or more steps from another method described herein.

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the foregoing has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges, or steps to those claimed, whether or not such alternate, interchangeable and/or equivalent structures, functions, ranges or steps are disclosed herein, and without intending to publicly dedicate any patentable subject matter.

What is claimed is:

1. A system, comprising:
a device comprising:
a signal generator; and
at least one processor configured to:
monitor a value of a medical parameter of a patient that is associated with type 2 diabetes, a condition of metabolic syndrome, pancreatis, or any combination thereof;
determine one or more stimulation parameters for stimulating at least one spinal nerve of the patient with an electrical signal;
select, from a group of electrodes, one or more stimulating electrodes which maximize at least one characteristic of measured compound action potentials (CAPs), wherein unselected electrodes in the group of electrodes are non-stimulating electrodes; and
control the signal generator to generate the electrical signal based on the one or more stimulation parameters, the electrical signal being introduced to the at least one spinal nerve by the one or more stimulating electrodes, which causes a response by at least one anatomical element of the patient that changes the value of the medical parameter for the patient.

2. The system of claim 1, wherein the at least one processor is configured to control the signal generator to generate the electrical signal when the value of the medical parameter is not within an acceptable range of values, and to control the signal generator to cease generating the electrical signal when the value of the medical parameter is within the acceptable range of values.

3. The system of claim 1, wherein the at least one processor controls the signal generator to generate the electrical signal in a manner that keeps the value of the medical parameter within an acceptable range of values.

4. The system of claim 1, wherein the medical parameter being monitored comprises a blood glucose level of the patient, an inflammatory marker associated with pancreatis, or both.

5. The system of claim 1, wherein the at least one processor is configured to select the one or more stimulation parameters further based on activity information about activity of the patient that is known to affect the value of the medical parameter.

6. The system of claim 5, wherein the activity information includes information about past patient activity, current patient activity, predicted patient activity, or any combination thereof.

7. The system of claim 6, wherein the past patient activity includes patient intake of food or patient intake of a drug, wherein the current patient activity includes current patient exercise, and wherein the predicted patient activity includes predicted patient exercise and predicted patient intake of food or predicted patient intake of a drug.

8. The system of claim 1, wherein the maximized at least one characteristic of measured CAPs includes CAP conduction velocity and CAP signal amplitude.

9. The system of claim 8, wherein the group of electrodes are included on different paddle leads, and wherein the at least one processor executes the following algorithm to select the one or more stimulating electrodes:

```
for each paddle lead (1 to x)
for each electrode (1 to n)
  y(ii)=function measure conduction velocity( );
  z(ii)=function measure CAP amplitude( )
end for each electrode
end (for each paddle lead)
function find maximum (y, z).
```

10. The system of claim 9, wherein the measurements of CAP conduction velocity and CAP signal amplitude are vectorized measurements.

11. The system of claim 8, wherein the one or more stimulating electrodes are selected from the group of electrodes further based on a detected patient position.

12. The system of claim 1, further comprising:

the group of electrodes; and a monitoring device configured to provide data that enables the at least one processor to monitor the value of the medical parameter.

13. The system of claim 1, wherein the one or stimulation parameters are selected from a list of stimulation parameters, and wherein the one or more stimulation parameters comprise values for duty cycle of the electrical signal, current level of the electrical signal, frequency of the electrical signal, pulse width of the electrical signal, or any combination thereof.

14. The system of claim 1, wherein the at least one spinal nerve comprises one or more dorsal root ganglions at one or more of thoracic levels T6 thru L2 of the patient, wherein the medical parameter being monitored is a glucose level, an inflammatory marker associated with pancreatis, or both, and wherein the response by the anatomical element causes reduction of the glucose level, the inflammatory marker, or both.

15. The system of claim 1, wherein the at least one spinal nerve comprises one or more dorsal root ganglions at one or more of thoracic levels T7 thru T12 of the patient, wherein the medical parameter being monitored is one of a glucose level, a triglyceride level, or a cholesterol level, and wherein the response by the anatomical element causes reduction of the glucose level, the triglyceride level, or the cholesterol level.

16. The system of claim 1, wherein the response by the anatomical element comprises an increase in insulin production, an increase in urinary excretion, or both.

17. A system for treating type 2 diabetes, comprising:

a device comprising:

a signal generator; and at least one processor configured to:

monitor a value of a medical parameter of a patient that is associated with type 2 diabetes;

determine one or more stimulation parameters for stimulating at least one spinal nerve of the patient with an electrical signal;

select, from a group of electrodes, one or more stimulating electrodes which maximize at least one characteristic of measured compound action potentials (CAPs), wherein unselected electrodes in the group of electrodes are non-stimulating electrodes; and control the signal generator to generate the electrical signal based on the one or more stimulation parameters, the electrical signal being introduced to the at least one spinal nerve by the one or more stimulating electrodes, which causes a response by at least one anatomical element of the patient that changes the value of the medical parameter for the patient.

18. The system of claim 17, wherein the at least one spinal nerve comprises one or more dorsal root ganglions at thoracic level T9 or T10 of the patient.

19. A system for treating metabolic syndrome, comprising:

a signal generator; and at least one processor configured to:

monitor a value of a medical parameter of a patient that is associated with metabolic syndrome;

determine one or more stimulation parameters for stimulating at least one spinal nerve of the patient with an electrical signal;

select, from a group of electrodes, one or more stimulating electrodes which maximize at least one characteristic of measured compound action potentials (CAPs), wherein unselected electrodes in the group of electrodes are non-stimulating electrodes; and control the signal generator to generate the electrical signal based on the one or more stimulation parameters, the electrical signal being introduced to the at least one spinal nerve by the one or more stimulating electrodes, which causes a response by at least one anatomical element of the patient that changes the value of the medical parameter for the patient.

20. The system of claim 19, wherein the medical parameter being monitored comprises a level of a lipid level of the patient.

* * * * *